(12) United States Patent
Tao et al.

(10) Patent No.: US 10,718,011 B2
(45) Date of Patent: Jul. 21, 2020

(54) SINGLE MOLECULE ELECTRONIC MULTIPLEX SNP ASSAY AND PCR ANALYSIS

(71) Applicant: THE TRUSTEES OF COLUMBIA UNIVERSITY IN THE CITY OF NEW YORK, New York, NY (US)

(72) Inventors: Chuanjuan Tao, New York, NY (US); Shiv Kumar, Belle Mead, NJ (US); Minchen Chien, Tenafly, NJ (US); Jingyue Ju, Englewood Cliffs, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 298 days.

(21) Appl. No.: 15/118,812

(22) PCT Filed: Feb. 12, 2015

(86) PCT No.: PCT/US2015/015647
§ 371 (c)(1),
(2) Date: Aug. 12, 2016

(87) PCT Pub. No.: WO2015/123430
PCT Pub. Date: Aug. 20, 2015

(65) Prior Publication Data
US 2017/0058335 A1    Mar. 2, 2017

Related U.S. Application Data

(60) Provisional application No. 61/939,144, filed on Feb. 12, 2014.

(51) Int. Cl.
*C12Q 1/6858*   (2018.01)
*C12Q 1/6853*   (2018.01)

(52) U.S. Cl.
CPC ......... *C12Q 1/6858* (2013.01); *C12Q 1/6853* (2013.01); *C12Q 2525/186* (2013.01); *C12Q 2565/631* (2013.01)

(58) Field of Classification Search
None
See application file for complete search history.

(56) References Cited

U.S. PATENT DOCUMENTS

2012/0046178 A1* 2/2012 Van Den Boom ... C12Q 1/6809
506/4

OTHER PUBLICATIONS

Kumar et al., "PEG-Labeled Nucleotides and Nanopore Detection for Single Molecule DNA Sequencing by Synthesis," Scientific Reports, September, vol. 2, No. 684, pp. 1-8. (Year: 2012).*

* cited by examiner

*Primary Examiner* — Young J Kim
(74) *Attorney, Agent, or Firm* — John P. White; Gary J. Gershik; Cooper & Dunham LLP

(57) ABSTRACT

This invention provides methods of using labeled primers or probes for nucleic acid target detection and to detect the identity or presence of a nucleotide at certain positions in nucleic acid sequences with single molecule sensitivity using nanopore detection, and sets of oligonucleotide primers for use in such methods, as well as methods of quantitative PCR coupled with nanopore detection.

18 Claims, 11 Drawing Sheets

Specification includes a Sequence Listing.

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: synthesized oligonucleotide

<400> SEQUENCE: 1
cagatgatat gttctaattc                                              20

<210> SEQ ID NO 2
<211> LENGTH: 20
<212> TYPE: DNA
<213> ORGANISM: Artificial
<220> FEATURE:
<223> OTHER INFORMATION: synthesized oligonucleotide

<400> SEQUENCE: 2
tcacaaagtg tatttagccg                                              20

<210> SEQ ID NO 3
<211> LENGTH: 20
<212> TYPE: DNA
<213> ORGANISM: Artificial
<220> FEATURE:
<223> OTHER INFORMATION: synthesized oligonucleotide directed to
      retinoblastoma 1 tumor suppressor gene

<400> SEQUENCE: 3
cagatgatat gttctaatta                                              20

<210> SEQ ID NO 4
<211> LENGTH: 20
<212> TYPE: DNA
<213> ORGANISM: Artificial
<220> FEATURE:
<223> OTHER INFORMATION: synthesized oligonucleotide

<400> SEQUENCE: 4
gagataggct agccgataca                                              20

<210> SEQ ID NO 5
<211> LENGTH: 20
<212> TYPE: DNA
<213> ORGANISM: Artificial
<220> FEATURE:
<223> OTHER INFORMATION: synthesized oligonucleotide

<400> SEQUENCE: 5
cagatgatat gttctaatta                                              20

<210> SEQ ID NO 6
<211> LENGTH: 20
<212> TYPE: DNA
```

```
<213> ORGANISM: Artificial
<220> FEATURE:
<223> OTHER INFORMATION: synthesized oligonucleotide

<400> SEQUENCE: 6
cagatgatat gttctaattt                                              20

<210> SEQ ID NO 7
<211> LENGTH: 20
<212> TYPE: DNA
<213> ORGANISM: Artificial
<220> FEATURE:
<223> OTHER INFORMATION: synthesized oligonucleotide

<400> SEQUENCE: 7
cagatgatat gttctaattg                                              20

<210> SEQ ID NO 8
<211> LENGTH: 41
<212> TYPE: DNA
<213> ORGANISM: Homo sapiens

<400> SEQUENCE: 8
tagcctatct acggctaaat acactttgtg aacgccttct g                      41
```

SINGLE MOLECULE ELECTRONIC MULTIPLEX SNP ASSAY AND PCR ANALYSIS

CROSS-REFERENCE TO RELATED APPLICATIONS

This application is a § 371 national stage of PCT International Application No. PCT/US2015/015647, filed Feb. 12, 2015, claiming the benefit of U.S. Provisional Application No. 61/939,144, filed Feb. 12, 2014, the content of each of which is hereby incorporated by reference into the application.

REFERENCE TO A SEQUENCE LISTING

This application incorporates-by-reference nucleotide and/or amino acid sequences which are present in the file named "160812_86100-PCT-US_Substitute_Sequence_Listing_CAE.txt", which is 1.87 kilobytes in size, and which was created Aug. 11, 2016 in the IBM-PC machine format, having an operating system compatibility with MS-Windows, which is contained in the text file filed Aug. 12, 2016 as part of this application.

Throughout this application, various publications are referenced. Full citations for these references may be found at the end of the specification immediately preceding the claims. The disclosures of these publications in their entirety are hereby incorporated by reference into this application to more fully describe the state of the art to which this invention pertains.

BACKGROUND OF THE INVENTION

A single nucleotide polymorphism (SNP) is a single base variation in the genome of a living organism. SNPs may occur in coding sequences of genes and non-coding regions of genes, including regulatory regions. SNPs in the coding sequences of the genome are classified as two types: synonymous and nonsynonymous. Synonymous SNPs do not alter the protein sequence due to the degeneracy of the genetic code, while nonsynonymous SNPs change the amino acid sequence of the encoded protein. The nonsynonymous SNPs are further divided into two types: missense and nonsense. A missense mutation is a single nucleotide point mutation leading to a codon that codes for a different amino acid compared to the wild-type, whereas a nonsense mutation is a point mutation that results in a premature stop codon. SNPs that are not in protein-coding regions can impact the function of the genes by altering splicing sequences and binding activity of transcription factors as well as gene expression. Among all the genetic variations, SNPs are the most common genetic differences between human beings. Over 3.1 million SNPs have been characterized from the human genome in a second-generation human haplotype map (Frazer et al. 2007). Thus, SNPs are important biomarkers for investigating the molecular basis underlying the mechanism for disease development, laying a foundation for precision medicine.

The Human Genome Project and the construction of a comprehensive human genome sequence map (Lander et al. 2001, Venter et al. 2001, and Wheeler et al. 2008) provide valuable resources for the study of genetic variations. These genetic differences include SNPs, gene copy number variations, insertions and deletions. SNPs have been established as unique biomarkers for the discovery and characterization disease genes (Kwok 2000 and Roses 2000). These research efforts require the characterization of large number of SNPs with technologies that are cost-effective and high-throughput with high-accuracy. The following DNA sequencing platforms are widely used for characterizing genetic variations: (1) 4-color fluorescent Sanger method (Smith et al. 1986, Ju et al. 1995, Ju et al. 1996, Salas-Solano et al. 1998, and Kheterpal et al. 1996), (2) sequencing by synthesis (SBS) using cleavable fluorescent nucleotide reversible terminators (Ju et al. 2006 and Bentley et al. 2008), (3) SBS with detection of the chemiluminescent signals caused by the released pyrophosphate during polymerase reaction (pyrosequencing) (Margulies et al. 2005), (4) SBS with electronic detection of the released proton during polymerase reaction (ion torrent sequencing) (Rothberg et al. 2011), and (5) single molecule fluorescent SBS methods (Harris et al. 2008 and Eid et al. 2009). However, these sequencing technologies are not designed for pinpoint detection of SNPs, and are still too costly for performing large scale SNP studies. Matrix assisted laser desorption/ionization time-of-flight mass spectrometry (MALDI-TOF MS) and fluorescence emission are two dominant detection methods for SNP analysis. SNP assay approaches using the above two detection methods are reviewed below.

SNP Analysis by MALDI-TOF MS Detection

MALDI-TOF MS measures the mass of the target molecules with highly accurate results in a digital format. It has been used for SNP detection by single base extension (SBE) (Haff et al. 1997, Tang et al. 1999, Ross et al. 1998, Fei et al. 1998, and Griffin et al. 2000), hybridization (Stoerker et al. 2000 and Ross et al. 1997), and invasive cleavage (Griffin et al. 1999 and Lyamichev et al. 1999). MALDI-TOF MS has also been used for gene expression analysis and single-copy DNA haplotyping in the context of nucleotide extension by polymerase (Ding et al., PNAS 100:3059-3064, 2003 and Ding et al., PNAS 100:7449-7453 2003).

Most multiplex SNP analyses make use of the specificity of the SBE reaction catalyzed by polymerase. One of the widely used SNP characterization method utilizes SBE and MALDI-TOF MS detection. In this approach, oligonucleotide primers are designed and synthesized based on the genetic variation in the target gene. The 3'-end of the primer anneals immediately next to a SNP site of the DNA template. A single dideoxynucleotide that is complementary to the SNP site is then incorporated into the primer by DNA polymerase. The identity of the SNP is determined by the mass of the resulting primer extension product obtained from the MALDI-TOF MS spectrum.

SNP Analysis by Fluorescence Detection

Numerous SNP genotyping methods have been developed using fluorescence labeling and detection, including microarray (Hartmann et al. 2009), PCR-RFLP analysis (Chowdhury et al. 2007), and TaqMan real-time genotyping (Bai et al. 2004). There are several advantages to using fluorescence labeling and detection, which include a variety of robust chemical coupling methods to tag the target molecules, high detection sensitivity of several photophysical parameters (life time, emission and polarization) and the capability of multiplexing. The molecular inversion probe (MIP) approach has been developed for SNP detection (Hardenbol et al. 2003). In this method, successive extension and ligation of locus-specific DNA probes yields a circular shape at polymorphic sites of the target gene. The linear probes are then selectively degraded, whereas the circular DNA probes that contain allelic information are amplified and analyzed using a microarray with fluorescence detection. Using this approach, Hardenbol et al. (2003) performed genotyping of more than 1,000 SNPs per assay.

The HIP method has the advantage of a very high level of multiplexing. However, many enzymatic reaction steps and complicated probe design are required for NIP.

Prior multiplex SNP assays primarily used either mass spectrometric detection or fluorescent tags and optical detection. None of these previous assays offer single molecule detection sensitivity and all require bulky instruments. None used nanopores to identify molecular or polymer tags corresponding to nucleotides of interest or SNPs, so as to identify the nucleotides of interest or SNPs.

SUMMARY OF THE INVENTION

This invention provides a method for identifying a single nucleotide residue of interest at a position within a stretch of consecutive nucleotide residues in a DNA, comprising the steps of:
  (a) incubating the DNA with
    (1) at least one oligonucleotide primer, each primer comprising a removably attached label (i) corresponding to a particular primer sequence, and (ii) having a unique signature detectable by a nanopore, wherein the nucleotides in the primer that are 5' to the nucleotide at the 3'-terminus of the primer are substantially fully complementary to the nucleotides in the DNA immediately 3' to the single nucleotide of interest,
    (2) terminating nucleotides, and
    (3) DNA polymerase,
  so as to perform a single base extension of a primer whose 3' terminal nucleotide hybridized to the single nucleotide residue of interest in the DNA, if such a primer was present, using the terminating nucleotide, thereby forming an extension product of the primer which had a 3' nucleotide complementary to the nucleotide of interest in the DNA;
  (b) removing the label from the extension product, if present;
  (c) detecting by nanopore the signature of the label of the primer whose 3' terminal nucleotide hybridized to the single nucleotide residue of interest, so as to identify the label and primer, if present;
thereby identifying the single nucleotide residue of interest.

In an embodiment of the instant method, in step (a) the DNA is incubated with a plurality of oligonucleotide primers, wherein the plurality of oligonucleotide primers comprises at least two primers having (i) identical nucleotide sequences except for having a different nucleotide at the 3' terminus of each of the two primers, wherein the identical nucleotides in each of the two primers are substantially fully complementary to the nucleotides in the DNA immediately 3' to the single nucleotide residue of interest.

This invention also provides for an assay for performing the instant method.

This invention also provides for a set of oligonucleotide primers, wherein each primer comprises a removably attached label (1) corresponding to a particular primer sequence, and (2) having a unique signature detectable by a nanopore, wherein the set comprises at least two primers having (i) identical nucleotide sequences except for having a different nucleotide at the 3' terminus of each of the two primers, and (ii) a different label corresponding to the different nucleotide at the 3' terminus, wherein the identical nucleotides in each of the two primers are substantially fully complementary to the nucleotides in a strand of DNA immediately 3' to a single nucleotide residue of interest.

This invention also provides for a set of oligonucleotide primers, wherein each primer comprises a removably attached label (1) corresponding to a particular primer sequence, and (2) having a unique signature detectable by a nanopore; and wherein the 3' nucleotide of each primer is complementary to a single nucleotide residue of interest in a strand of DNA and the other nucleotides in that primer are substantially fully complementary to the nucleotides in the DNA immediately 3' of the single nucleotide residue of interest.

This invention also provides for a method for simultaneously detecting in a sample the presence of one or more of a plurality of different target nucleic acids comprising the steps of:
  (a) contacting the sample with a plurality of nucleic acid primers simultaneously and under conditions permitting, and for a time sufficient for, primer extension to occur, wherein (i) for each target nucleic acid at least one predetermined primer is used which corresponds to that target nucleic acid, and (ii) each primer has a removably attached label having a unique signature detectable by a nanopore;
  (b) separating any unextended primers from any extended primers;
  (c) simultaneously removing the labels from any extended primers; and
  (d) detecting the presence of any labels so removed;
wherein the presence of a removed label having a signature identical to the label removably attached to a predetermined primer indicates the presence in the sample of the target nucleic acid specifically recognized by that predetermined primer.

This invention also provides for a method of identifying or quantifying a target nucleic acid, comprising the steps of:
  (a) incubating the target nucleic acid with a probe, wherein the probe comprises (i) a nucleotide sequence that is fully substantially complementary to the target nucleic acid, and (ii) an attached label having a unique signature detectable by a nanopore, in conditions permitting the probe to hybridize to the target nucleic acid;
  (b) performing PCR;
  (c) releasing the label from the probe;
  (d) detecting by nanopore an electronic change caused by the label; and
  (e) correlating the amplitude of the electronic change determined in step (d) with the quantity of label,
thereby identifying or quantifying the target nucleic acid.

DETAILED DESCRIPTION OF THE INVENTION

Figure 1:
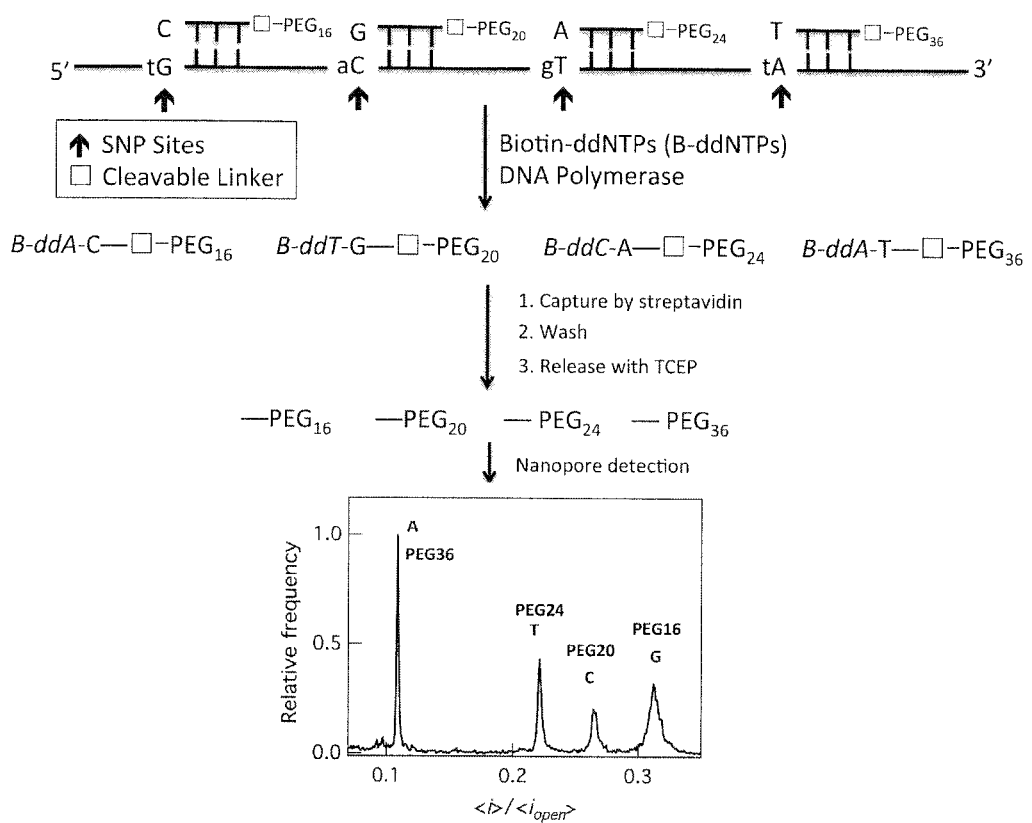
FIG. 1. Single molecule electronic multiplex SNP (SM-EMS) assay scheme using cleavable PEG-labeled primers and biotinylated dideoxynucleotides (B-ddNTPs). A library of PEG-labeled primers annealed to the DNA template containing the SNP sites are incubated with B-ddNTPs and DNA polymerase. The nucleotide at the 3'-end of each PEG-labeled primer is complementary to a particular SNP in the template. Only the perfectly complementary, cleavably PEG-labeled primer is extended by polymerase with a B-ddNTP. The streptavidin-coated magnetic beads only capture the biotinylated DNA extension products from the PEG-labeled primer while the other components in the polymerase reaction are washed away. Treatment of the captured DNA products with TCEP cleaves the PEGs, which are analyzed by nanopore to yield unique electrical current blockade signatures, each of which determines a unique SNP.

While various embodiments of the invention have been shown and described herein, it will be obvious to those skilled in the art that such embodiments are provided by way of example only. Numerous variations, changes, and substitutes may occur to those skilled in the art without departing from the invention. It should be understood that various alternatives to the embodiments of the invention described herein may be employed.

TERMS

As used herein, and unless stated otherwise, each of the following terms shall have the definition set forth below.
A—Adenine;
C—Cytosine;
DNA—Deoxyribonucleic acid;
G—Guanine;
RNA—Ribonucleic acid;
T—Thymine; and
U—Uracil.

The articles "a", "an" and "the" are non-limiting. For example, "the method" includes the broadest definition of the meaning of the phrase, which can be more than one method.

"Signature" of a compound in a pore shall include, for example, a signal or change occurring when the compound passes through or interacts with the pore. One such change may be an electronic signature.

"Electronic signature" of a nucleotide or other molecules, such as labels and polymer tags, passing through a pore via application of an electronic field shall include, for example, the duration of the nucleotide's or molecule's passage through the pore together with the observed amplitude of current during that passage. Electronic signatures can be visualized, for example, by a plot of current (e.g. pA) versus time. Electronic signature for a DNA is also envisioned and can be, for example, a plot of current (e.g. pA) versus time for the DNA to pass through the pore via application of an electric field.

"Nanopore" includes, for example, a structure comprising (a) a first and a second compartment separated by a physical barrier, which barrier has at least one pore with a diameter, for example, of from about 1 to 10 nm, and (b) a means for applying an electric field across the barrier so that a charged molecule such as DNA can pass from the first compartment through the pore to the second compartment. The nanopore ideally further comprises a means for measuring the electronic signature of a molecule passing through its barrier. The nanopore barrier may be synthetic or naturally occurring, or both, in part. Barriers can, for example, be biological, comprising naturally-occurring compounds or materials derived from such compounds. This includes, for example, lipid bilayers having therein α-hemolysin, oligomeric protein channels such as porins, and synthetic peptides and the like. Barriers can also be, for example, solid state nanopores including, for example, inorganic plates having one or more holes of a suitable size. Herein "nanopore", "nanopore barrier" and the "pore" in the nanopore barrier are sometimes used equivalently.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Hybridize" shall mean the annealing of one single-stranded nucleic acid (such as primer) to another nucleic acid based on the well-understood principle of sequence complementarity. In an embodiment the other nucleic acid is a single-stranded nucleic acid. The propensity for hybridization between nucleic acids depends on the temperature and ionic strength of their miliu, the length of the nucleic acids and the degree of complementarity. The effect of these parameters on hybridization is described in, for example, Sambrook J, Fritsch E F, Maniatis T., Molecular cloning: a laboratory manual, Cold Spring Harbor Laboratory Press, New York (1989). As used herein, hybridization of a primer sequence, or of a DNA extension product, respectively, is extendable by creation of a phosphodiester bond with an available nucleotide or nucleotide analogue capable of forming a phosphodiester bond, therewith.

"Primer" as used herein (a primer sequence) is a short, usually chemically synthesized oligonucleotide, of appropriate length, for example about 18-24 bases, sufficient to hybridize to a target DNA (e.g. a single stranded DNA) and permit the addition of a nucleotide residue thereto, or oligonucleotide or polynucleotide synthesis therefrom, under suitable conditions well-known in the art. In an embodiment the primer is a DNA primer, i.e. a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product.

"Terminating nucleotide" shall mean any modified or unmodified nucleotide which, when incorporated into a nucleotide strand, prevents or severely hampers further elongation of the nucleotide strand. One example is a dideoxynucleotide. A terminating nucleotide may comprise a hook.

"Hook", as used herein with respect to a terminating nucleotide, shall refer to any chemical moiety that may bind to, react with, or be captured by another chemical moiety, compound, or material, having a high affinity for the hook. One example of a hook is biotin, which interacts strongly with streptavidin. Another example is phenylboronic acid (PBA), which interacts strongly with salicylhydroxamic acid (SHA).

As used herein, "substantially identical" or "substantially fully complementary" sequences have at least about 80% sequence identity or complementarity, respectively, to a nucleotide sequence. Substantially identical sequences or substantially fully complementary sequences may have at least about 85%, 90%, 95% or 100% sequence identity or complementarity, respectively.

Principle of Single Molecule Electronic Multiplex SNP Assay

The principle of the single molecule electronic multiplex SNP (SM-EMS) assay is described as follows (FIG. 1). A library of oligonucleotide primers corresponding to different SNP sites of a target gene are labeled with PEGs of different sizes through an azido-based linker that can be efficiently cleaved by tris-(2-carboxyethyl)phosphine (TCEP). The azido-based linker has been successfully used to construct nucleotide reversible terminators for sequencing by synthesis (Guo et al. 2008) and cleavable biotinylated dideoxynucleotides for DNA sequencing and SNP analysis by MALDI-TOF MS (Qiu et al., Biochem 427:193-201, 2012). The nucleotide at the 3'-end of each PEG-labeled oligonucleotide primer is complementary to a particular SNP in the DNA template. Single base extension in a single tube is performed using the cleavable PEG-labeled primers and biotinylated dideoxynucleotides (biotin-ddNTPs) and DNA polymerase. Only the PEG-labeled primer that is fully complementary to the DNA template is extended by DNA polymerase with a biotin-ddNTP. The PEG-labeled DNA extension products that carry a biotin at the 3'-end is subsequently captured with streptavidin-coated magnetic beads; the unextended PEG-labeled primers and other components of the SBE reaction are eliminated by washing. Treatment of the captured DNA products with TCEP cleaves the azido-based linker to release the PEGs, which are analyzed by nanopore. Each different-sized PEG produces a unique nanopore electrical current blockade signature at single molecule level analogous to that of single molecule electronic sequencing by synthesis (Kumar et al. 2012), which leads to the identification of the SNP (FIG. 1). Thus, the use of PEG-labeled primers and biotin-ddNTPs coupled with the specificity of DNA polymerase in SBE will yield a multiplex method for detecting SNPs electronically with single molecule sensitivity.

A non-limiting example of a set of oligonucleotide primers that could be used in such a method is

```
                                            (SEQ ID NO: 1)
       5'-W-CAGATGATATGTTCTAATTC-3';

(SEQ ID NO: 2)
       5'-X-TCACAAAGTGTATTTAGCCG-3';

(SEQ ID NO: 3)
       5'-Y-CAGATGATATGTTCTAATTA-3';
       and (SEQ ID NO: 4)
       5'-Z-GAGATAGGCTAGCCGATACA-3',
``` wherein in each primer, the 3' nucleotide is complementary to a nucleotide found at a site of interest (or SNP site), and the remaining nucleotides in the primer are complementary to the nucleotides that are 3' to the nucleotide found at a site of interest (or SNP site), and W, X, Y, and Z are labels having unique signatures detectable by a nanopore. Such a set of four primers could be used to, for example, detect the presence of four SNPs simultaneously.

The above exemplary technique can be easily modified to identify single nucleotides at a given location. A library of primers is prepared, where there are at least two primers having labels with unique signatures detectable by a nanopore, with identical nucleic acid sequences except for the nucleotide at the 3' terminus, where the nucleotides in the primer that are 5' of the 3' nucleotide are substantially fully complementary to the nucleotides immediately 3' to the nucleotide of interest. These are brought in contact with a DNA strand containing the nucleotide of interest (also referred to as a template DNA), in the presence of, for example, biotinylated dideoxynucleotides and DNA polymerase, so as to allow a single base extension reaction to occur. The extension product can then be separated from the non-extended primers, and the label cleaved and identified via detection by nanopore, so as to identify the primer that was extended. If the primers were identical except for the nucleotide at the 3' terminus, which is known, the nucleotide at the 3' terminus can be readily determined by identification of the unique label, and this nucleotide will be complementary to the nucleotide of interest. This technique can be done, for example, with multiple sets of at least two uniquely-labeled primers, so as to identify multiple nucleotides of interest at once.

A non-limiting example of a set of oligonucleotide primers that could be used in such a method is

```
                                            (SEQ ID NO: 1)
       5'-W-CAGATGATATGTTCTAATTC-3';

(SEQ ID NO: 5)
       5'-X-CAGATGATATGTTCTAATTA-3';

(SEQ ID NO: 6)
       5'-Y-CAGATGATATGTTCTAATTT-3';
       and (SEQ ID NO: 7)
       5'-Z-CAGATGATATGTTCTAATTG-3',
``` wherein each primer has an identical sequence except for the 3'-terminal nucleotide, and the remaining nucleotides in each primer are complementary to the nucleotides that are 3' to the nucleotide found at a site of interest (or SNP site), and W, X, Y, and Z are labels having unique signatures detectable by a nanopore.

Embodiments of the Invention

This invention provides a method for identifying a single nucleotide residue of interest at a position within a stretch of consecutive nucleotide residues in a DNA, comprising the steps of:
 (a) incubating the DNA with
  (1) at least one oligonucleotide primer, each primer comprising a removably attached label (i) corresponding to a particular primer sequence, and (ii) having a unique signature detectable by a nanopore, wherein the nucleotides in the primer that are 5' to the nucleotide at the 3'-terminus of the primer are substantially fully complementary to the nucleotides in the DNA immediately 3' to the single nucleotide of interest,
  (2) terminating nucleotides, and
  (3) DNA polymerase,
  so as to perform a single base extension of a primer whose 3' terminal nucleotide hybridized to the single nucleotide residue of interest in the DNA, if such a primer was present, using the terminating nucleotide, thereby forming an extension product of the primer which had a 3' nucleotide complementary to the nucleotide of interest in the DNA;
 (b) removing the label from the extension product, if present;
 (c) detecting by nanopore the signature of the label of the primer whose 3' terminal nucleotide hybridized to the single nucleotide residue of interest, so as to identify the label and primer, if present;
thereby identifying the single nucleotide residue of interest.

In an embodiment of the instant method, the DNA is a single-stranded DNA. In another embodiment of the instant method, the DNA is a double-stranded DNA.

In an embodiment of the instant method, in step (a) the DNA is incubated with a plurality of oligonucleotide primers, wherein the plurality of oligonucleotide primers comprises at least two primers having (i) identical nucleotide sequences except for having a different nucleotide at the 3' terminus of each of the two primers, wherein the identical nucleotides in each of the two primers are substantially fully complementary to the nucleotides in the DNA immediately 3' to the single nucleotide residue of interest.

In another embodiment of the instant method, in step (a) the DNA is incubated with a plurality of oligonucleotide primers, wherein the plurality of oligonucleotide primers comprises at least three primers having (i) identical nucleotide sequences except for having a different nucleotide at the 3' terminus of each of the three primers, wherein the identical nucleotides in each of the three primers are substantially fully complementary to the nucleotides in the DNA immediately 3' to the single nucleotide residue of interest.

In another embodiment of the instant method in step (a) the DNA is incubated with a plurality of oligonucleotide primers, wherein the plurality of oligonucleotide primers comprises at least four primers having (i) identical nucleotide sequences except for having a different nucleotide at the 3' terminus of each of the four primers, wherein the identical nucleotides in each of the four primers are substantially fully complementary to the nucleotides in the single-stranded DNA immediately 3' to the single nucleotide residue of interest.

In another embodiment of the instant method, the terminating nucleotides are dideoxynucleotides.

In another embodiment of the instant method, the terminating nucleotides comprise a hook.

In another embodiment of the instant method, the hook is a biotin moiety.

In another embodiment of the instant method, the hook is a phenylboronic acid (PBA) moiety.

In another embodiment of the instant method, prior to removing the label, the extension product is separated from the unextended primers.

In another embodiment of the instant method, the extension product is separated from the unextended primers by capturing the extension product on streptavidin-coated magnetic beads;

In another embodiment of the instant method, the extension product is separated from the unextended primers by capturing the extension product on salicylhydroxamic acid (SHA)-coated magnetic beads;

In another embodiment of the instant method, the label is removably attached via a cleavable linker. In a further embodiment of the instant method, the cleavable linker is an azido-based linker. In a further embodiment of the instant method, the cleavable linker is cleaved in step (b) by a phosphine-containing moiety. In a further embodiment of the instant method, the cleavable linker is cleaved in step (b) by tris-(2-carboxyethyl)phosphine (TCEP). In a further embodiment of the instant method, the cleavable linker is attached to the 5'-terminus of the oligonucleotide primer between the label and the oligonucleotide.

In another embodiment of the instant method, the label comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

In another embodiment of the instant method, the labels are polyethylene glycol (PEG) labels. In a further embodiment of the instant method, the PEG labels each have a different length from each other.

In another embodiment of the instant method, the DNA is incubated with a plurality of primers, each primer comprising an attached label having a unique signature detectable by a nanopore. In a further embodiment of the instant method, at least 20 different oligonucleotide primers are incubated with the single-stranded DNA in step (a).

In an embodiment of the instant method, the nanopore is biological. In another embodiment of the instant method, the nanopore is proteinaceous. In a further embodiment of the instant method, the nanopore comprises alpha hemolysin. In another embodiment of the instant method, the nanopore is a solid-state nanopore. In another embodiment of the instant method, the nanopore is in a solid state membrane.

In an embodiment of the instant method, the signature is an electronic signature. In a further embodiment of the instant method, the signature is an electrical current blockade signature.

In an embodiment of the instant method, the nucleotide sequence of the portion of each primer which is 5' to the 3' nucleotide of the primer is at least 85% complementary to the sequence of the DNA which is 3' to the single nucleotide residue of interest.

In a further embodiment of the instant method, the nucleotide sequence of the portion of each primer which is 5' to the 3' nucleotide of the primer is at least 90% complementary to the sequence of the DNA which is 3' to the single nucleotide residue of interest.

In a further embodiment of the instant method, the nucleotide sequence of the portion of each primer which is 5' to the 3' nucleotide of the primer is at least 95% complementary to the sequence of the DNA which is 3' to the single nucleotide residue of interest.

In a further embodiment of the instant method, the nucleotide sequence of the portion of each primer which is 5' to the 3' nucleotide of the primer is 100% complementary to the sequence of the DNA which is 3' to the single nucleotide residue of interest.

In another embodiment of the instant method, the sequence of the primer is 10-40 nucleotides long. In a further embodiment of the instant method, the sequence of the primer is 18-24 nucleotides long.

In an embodiment of the instant method, the single nucleotide of interest is at the site of a single nucleotide polymorphism (SNP).

This invention also provides for an assay for performing any of the instant methods.

This invention also provides for a set of oligonucleotide primers, wherein each primer comprises a removably attached label (1) corresponding to a particular primer sequence, and (2) having a unique signature detectable by a nanopore, wherein the set comprises at least two primers having (i) identical nucleotide sequences except for having a different nucleotide at the 3' terminus of each of the two primers, and (ii) a different label corresponding to the different nucleotide at the 3' terminus, wherein the identical nucleotides in each of the two primers are substantially fully complementary to the nucleotides in a strand of DNA immediately 3' to a single nucleotide residue of interest.

In a further embodiment of the instant set of oligonucleotide primers, the set comprises at least three primers having (i) identical nucleotide sequences except for having a different nucleotide at the 3' terminus of each of the three primers, and (ii) a different label corresponding to the different nucleotide at the 3' terminus, wherein the identical nucleotides in each of the three primers are substantially fully complementary to the nucleotides in the strand of DNA immediately 3' to a single nucleotide residue of interest.

In a further embodiment of the instant set of oligonucleotide primers, the set comprises at least four primers having (i) identical nucleotide sequences except for having a different nucleotide at the 3' terminus of each of the four primers, and (ii) a different label corresponding to the different nucleotide at the 3' terminus, wherein the identical nucleotides in each of the four primers are substantially fully complementary to the nucleotides in the strand of DNA immediately 3' to a single nucleotide residue of interest.

This invention also provides for a set of oligonucleotide primers, wherein each primer comprises a removably attached label (1) corresponding to a particular primer sequence, and (2) having a unique signature detectable by a nanopore; and wherein the 3' nucleotide of each primer is complementary to a single nucleotide residue of interest in a strand of DNA and the other nucleotides in that primer are substantially fully complementary to the nucleotides in the DNA immediately 3' of the single nucleotide residue of interest.

In a further embodiment of the instant sets of oligonucleotide primers, the single nucleotide residue of interest is at a site of a single nucleotide polymorphism (SNP).

In a further embodiment of the instant sets of oligonucleotide primers, the sequence of each primer is 15-40 nucleotides long. In a further embodiment of the sets of oligonucleotide primers, the sequence of each primer is 18-24 nucleotides long.

In another embodiment of the instant sets of oligonucleotide primers, each removably attached label comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

In another embodiment of the instant sets of oligonucleotide primers, the removably attached labels are PEG labels, each having different lengths from each other.

This invention also provides for a method for simultaneously detecting in a sample the presence of one or more of a plurality of different target nucleic acids comprising the steps of:

(a) contacting the sample with a plurality of nucleic acid primers simultaneously and under conditions permitting, and for a time sufficient for, primer extension to occur, wherein (i) for each target nucleic acid at least one predetermined primer is used which corresponds to that target nucleic acid, and (ii) each primer has a removably attached label having a unique signature detectable by a nanopore;

(b) separating any unextended primers from any extended primers;

(c) simultaneously removing the labels from any extended primers; and (d) detecting the presence of any labels so removed;

wherein the presence of a removed label having a signature identical to the label removably attached to a predetermined primer indicates the presence in the sample of the target nucleic acid specifically recognized by that predetermined primer.

In a further embodiment of the instant method, at least two different primers correspond to the same target nucleic acid. In a further embodiment of the instant method, a first primer is a forward primer for the target nucleic acid and a second primer is a reverse primer for the same target nucleic acid. In a further embodiment of the instant method, the labels attached to the first and second primers have the same signature. In another embodiment of the instant method, the labels attached to the first and second primers have different signatures.

In an embodiment of the instant method, the method detects the presence in the sample of 10 or more different target nucleic acids. In further embodiments of the instant method, the method detects the presence in the sample of 50 or more, 100 or more, or 200 or more different target nucleic acids.

In an embodiment of the instant method, the sample is contacted with 4 or more different primers. In further embodiments of the instant method, the sample is contacted with 10 or more, 50 or more, 100 or more, or 200 or more different primers.

In an embodiment of the instant method, the label is removed in step (d) by photocleaving. In a further embodiment of the instant method, the label is photocleaved in step (d) with ultraviolet light. In another embodiment of the instant method, the label is removed in step (d) by chemical cleaving.

In another embodiment of the instant method, each removably attached label comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

In an embodiment of the instant method, the labels are polyethylene glycol (PEG) labels. In a further embodiment of the instant method, the PEG labels are of different lengths.

In an embodiment of the instant method, the nanopore is biological. In another embodiment of the instant method, the nanopore is proteinaceous. In a further embodiment of the instant method, the nanopore comprises alpha hemolysin. In another embodiment of the instant method, the nanopore is a solid-state nanopore. In another embodiment of the instant method, the nanopore is in a solid state membrane.

In an embodiment of the instant method, the signature is an electronic signature. In a further embodiment of the instant method, the signature is an electrical current blockade signature.

This invention also provides for a method of identifying or quantifying a target nucleic acid, comprising the steps of:
 (a) incubating the target nucleic acid with a probe, wherein the probe comprises (i) a nucleotide sequence region that is fully substantially complementary to the target nucleic acid, and (ii) an attached label and having a unique signature detectable by a nanopore, in conditions permitting the probe to hybridize to the target nucleic acid;
 (b) performing PCR;
 (c) releasing the label from the probe;
 (d) detecting by nanopore an electronic change caused by the label; and
 (e) correlating the amplitude of the electronic change determined in step (d) with the quantity of label,
thereby quantifying the target nucleic acid.

In an embodiment of the instant method, the probe comprises a 5'-terminal region of nucleotides that does not hybridize to the target nucleic acid. In a further embodiment of the instant method, the 5'-terminal region of nucleotides that does not hybridize to the target nucleic acid is 3-15 nucleotides. In a further embodiment of the instant method, the 5'-terminal region of nucleotides that does not hybridize to the target nucleic acid is 5-10 nucleotides.

In an embodiment of the instant method, the probe's nucleotide sequence region that is fully substantially complementary to the target nucleic acid is 10-40 nucleotides. In a further embodiment of the instant invention, the probe's nucleotide sequence region that is fully substantially complementary to the target nucleic acid is 18-24 nucleotides.

In an embodiment of the instant method, the label is attached to the 5'-terminus of the probe.

In an embodiment of the instant method, the label comprises one or more of ethylene glycol, an amino acid, a carbohydrate, a peptide, a dye, a chemiluminiscent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

In an embodiment of the instant method, the label is a polyethylene glycol (PEG) label.

In an embodiment of the instant method, the PCR is performed using Taq polymerase. In another embodiment of the instant method, the polymerase activity of the polymerase during the PCR reaction causes the release of the label.

In an embodiment of the instant method, the nanopore is biological. In another embodiment of the instant method, the nanopore is proteinaceous. In a further embodiment of the instant method, the nanopore comprises alpha hemolysin. In another embodiment of the instant method, the nanopore is a solid-state nanopore. In another embodiment of the instant method, the nanopore is in a solid state membrane.

In an embodiment of the instant method, the signature is an electronic signature. In a further embodiment of the instant method, the signature is an electrical current blockade signature.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, a "$C_1$-$C_5$ alkyl" is defined to include groups having 1, 2, 3, 4, or 5 carbons in a linear or branched arrangement, and specifically includes methyl, ethyl, n-propyl, isopropyl, n-butyl, t-butyl, and pentyl As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_5$alkenyl" means an alkenyl radical having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_5$ alkynyl" means an alkynyl radical having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution (s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

Exemplary Labels

A label (or tag) may be any chemical group or molecule that is capable of being detected in a nanopore. In some cases, a label comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

In some cases, the label is a polymer. Polyethylene glycol (PEG) is an example of a polymer and has the following structure:

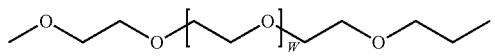

Any number of ethylene glycol units (W) may be used. In some cases, each label is a PEG label comprising a different number of ethylene glycol units.

Nanopore Detection of Labels

Previously, Kasianowicz et al. (1996) discovered that the α-hemolysin (αHL) protein nanopore, which has a 1.5 nm-diameter limiting aperture (Song et al. 1996, Bezrukov et al. 1996, Krasilnikov 2002, and Kasianowicz et al. 1995), could be used to electronically detect nucleic acids at the single molecule level. Thus, the αHL nanopore has been investigated widely for the development of a single molecule electronic DNA sequencing technology (Kasianowicz et al. 1996, Kasianowicz et al. 2002, Kasianowicz et al. 1998, and Clarke et al. 2009). The majority of these research efforts involve strand DNA sequencing by nanopore, which aim at sequencing DNA by threading it through the nanopore and detecting the electrical current blockade from the 4 nucleotides (A, C, G, T) (Cherf et al. 2012 and Manrao et al. 2012).

Figure 2:
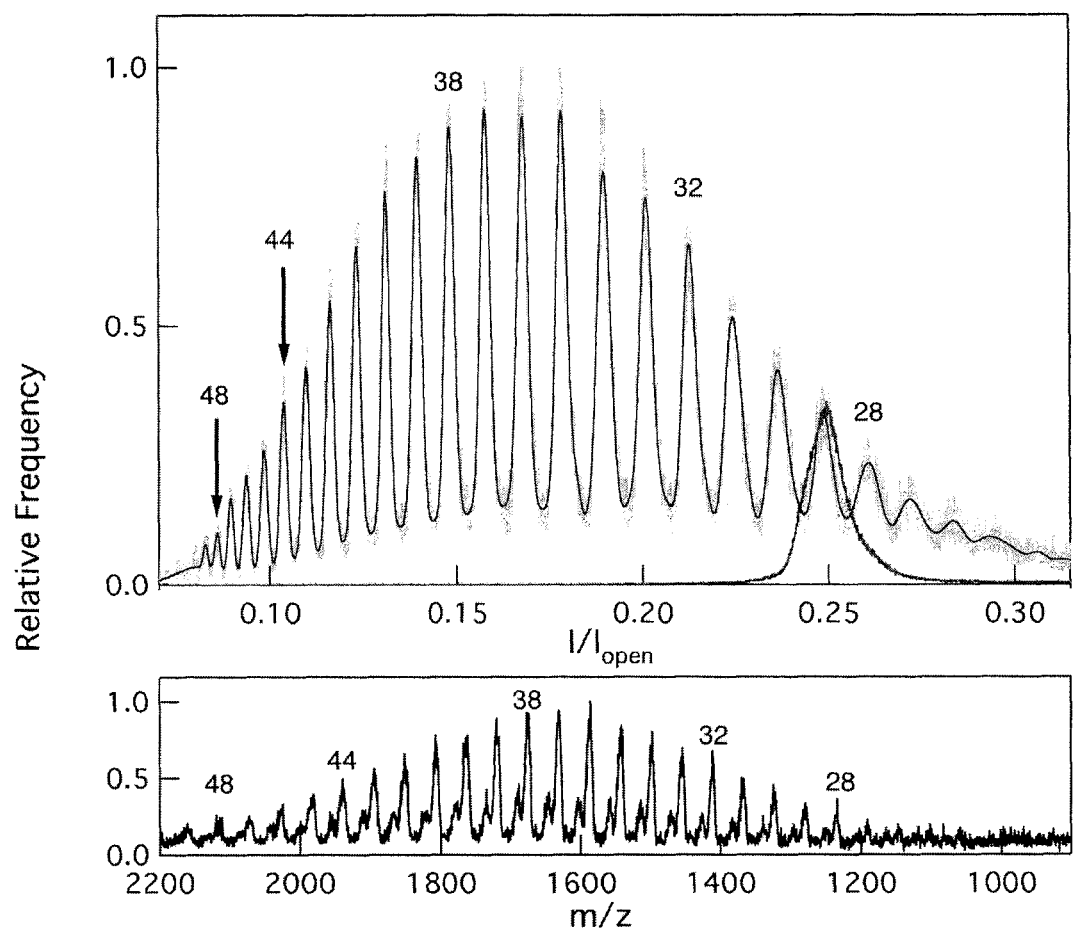
FIG. 2. Mass distributions of over 20 PEG polymers obtained with a single nanopore (upper) is compared with their corresponding MALDI-TOF mass spectrum (lower). The histogram (upper) indicates that PEG polymers differing by a single monomer unit can be detected and differentiated by nanopore at single molecule level electronically (adapted from Robertson, J. W. et al. 2007).

The native αHL nanopore has an intrinsic property for high-resolution discrimination of molecules and ions, which enables the discrimination between aqueous H and $D^+$ ions (Kasianowicz et al. 1995). Robertson et al. (2007) have demonstrated that the αHL nanopore can easily separate more than 20 different PEG polymers at single monomer level (FIG. 2). This study indicates that the mean residence time of the PEG polymer in the pore increases with its size (Reiner et al. 2010). Recently, Kumar et al. (2012) have reported the use of 4 PEGs of distinct size to label the terminal phosphate of nucleotides for single molecule electronic DNA sequencing by synthesis with nanopore detection. Based on these previous investigations, the proposed single molecule electronic multiplex SNP assay will be capable of detecting 20 genetic variations simultaneously using 20 PEGs of different sizes.

This invention will be better understood by reference to the Experimental Details which follow, but those skilled in the art will readily appreciate that the specific experiments are only illustrative of the invention as described more fully in the claims which follow thereafter. Every embodiment and feature described in the application should be understood to be interchangeable and combinable with every with embodiment contained within.

EXPERIMENTAL DETAILS AND DISCUSSION

Review of SNP Analysis Via MALDI-TOF MS

The early SBE method for multiplex SNP analysis using MALDI-TOF MS detected both primers and their extension products, because both were loaded to the MS analyzer. This requires the unambiguous simultaneous detection of multiplex primers and their extension products. However, for longer biopolymers, such as DNA, MALDI-TOF MS analyzer has limitations in resolution and sensitivity. As a result, larger DNA molecules could not be resolved by MALDI-TOF MS. To address this issue, Kim et al. developed a multiplex SNP assay (SPC-SBE) using solid phase capturable (SPC) biotinylated dideoxynucleotide terminators (biotin-ddNTPs) in SBE by detection with MALDI-TOF MS (Kim et al. 2002 and Kim et al. 2003).

In the SPC-SBE method, a library of oligonucleotide primers corresponding to the multiple SNP sites are designed to have different molecular mass. These primers are then annealed to the SNP sites of the target gene and extended with a specific biotin-ddNTP by DNA polymerase, producing 3'-biotinylated DNA products. Treatment of the polymerase reaction mixtures by streptavidin-coated magnetic beads leads to the capture of the DNA products that carry a biotin moiety at the 3'-end. The excess primers, DNA polymerase and salts in the reaction are washed away. The pure DNA extension products are subsequently released from the magnetic beads by denaturing the biotin-streptavidin interaction with formamide at 95° C., and characterized with MALDI-TOF MS for SNP determination. In the SPC-SBE approach, the accuracy and scope of multiplexing in SNP analysis is significantly increased, because only the isolated primer extension products are loaded into the MALDI-TOF MS analyzer. Consequently, the resulting mass spectrum is free of the non-extended primer peaks and their associated dimers, which do not carry a biotin moiety and are removed during SPC. SPC also facilitates desalting of the captured DNA products and therefore enhances the accuracy and the overall quality of the MS data for SNP analysis.

In summary, in the SPC-SBE multiplex SNP assay with MALDI-TOF MS (Kim et al. 2002), multiplex PCR products are produced as templates from genomic DNA for carrying out SBE reactions using SNP specific primers with different mass. Only the DNA extension products extended by a specific biotin-ddNTP are captured while the other components of the reaction are removed. DNA polymerase and biotin-ddNTPs. The captured DNA products are then released and loaded on to the MALDI-TOF MS analyzer to identify nucleotide variation. It has been shown that unextended primers occupy the effective mass range in the mass spectrum reducing the ability for multiplexing. The excess primers can form a dimer, producing false peaks in the mass spectrum (Roskey et al. 1996). All the above complications are completely removed by the SPC-SBE. Due to the large molecular weight difference of the four biotin-ddNTPs, polymerase extension products from these dideoxynucleotides are unambiguously detected with well resolved molecular weights. The molecular weight of the primer extension products in comparison to the masses of the corresponding primers reveal the identity of each nucleotide at the polymorphic site. The SPC-SBE method is particularly beneficial in determining heterozygous genotypes. In this case, two peaks, one corresponding to each allele, will be clearly discernible in the resulting mass spectrum.

MALDI-TOF MS, when used for characterizing SNPs, can simultaneously measure the masses of DNA molecules over a certain range. To make best use of this feature for the analysis of multiple SNPs in a single MS spectrum, if excess primers are not removed, masses of all primers and their extension products have to be sufficiently different to produce peaks that can be adequately resolved in the mass spectrum. For example, Ross et al. (1998) performed simultaneous detection of multiple SNPs by tuning the masses of all primers and their extension products so that they would lie in the range of 4.5 kDa and 7.6 kDa with no overlapping. In contrast, by eliminating the unextended primers that occupy the valuable mass range in the mass spectrum, the SPC-SBE approach significantly increases the scope of multiplexing in characterization of SNPs. Genetic variations (C282Y and H63D) in the human hereditary hemochromatosis gene were successfully and accurately characterized by SPC-SBE (Kim et al. 2002). Thirty polymorphic sites in exons 5, 7 and 8 of the tumor suppressor gene p53, which are most frequently mutated in human cancer (Hollstein et al. 1991 and Bardelli et al. 2003), from Wilms' tumors, head and neck squamous carcinomas as well as colorectal carcinomas, were also precisely determined with the SPC-SBE method (Kim et al. 2004). Using the SPC-SBE approach, Misra et al. performed concurrent analysis of 40 SNPs of CYP2C9 and 50 SNPs of CYP2A13 in the cytochrome P450 (CYP450) genes (Misra et al. 2007).

DNA purification exploiting the strong interaction of a small molecule, biotin, and a protein, streptavidin on solid surfaces such as magnetic beads is extensively used in biotechnology. However, the affinity between biotin and streptavidin is among the strongest known non-covalent bonds. The denaturing of the biotin-streptavidin interaction requires treatment with formamide at 95° C. and the reaction yield is often low. To further optimize the condition for SPC and release of the DNA extension products from streptavidin-coated magnetic beads, Qiu et al. (Anal. Biochem, 427:193-201, 2012) developed a set of chemically cleavable biotinylated dideoxynucleotides, ddNTPs-$N_3$-Biotin (ddATP-$N_3$-Biotin, ddGTP-$N_3$-Biotin, ddCTP-$N_3$-Biotin and ddUTP-$N_3$-Biotin), for application in DNA sequencing and SNP analysis by MALDI-TOF MS. These cleavable biotinylated dideoxynucleotides have been successfully used in SPC-SBE to characterize mitochondrial SNPs (Qiu et al., Anal. Biochem, 427:202-210, 2012).

Several alternative methods for multiplex SNP analysis that use mass spectrometry have been developed. For example, the commercially available MASSARRAY™ assay (Rodi et al. 2002) from Sequenom Inc. is widely used for characterizing genetic variations, including mitochondrial SNPs for population studies (Cerezo et al. 2009) and detection of heteroplasmy (Xiu-Cheng et al. 2008). The MASSARRAY™ assay is automated with high throughput. In one form of this approach, the primer is extended by DNA polymerase in the presence of three dideoxynucleotides and one deoxynucleotide that corresponds to one of the two alleles. At the end of the reaction, single nucleotide primer extension products and the primers extended with two or more nucleotides as well as the unextended primers are all loaded on to the MALDI-TOF MS analyzer and detected in the mass spectrum. Since no labeling of any reaction components is required, the MASSARRAY™ assay is simple to perform. However, it is limited in performing simultaneous high level multiplex analysis of SNPs, because all reaction products and all unextended primers are both loaded into the MS analyzer.

Review of SNP Analysis by Fluorescence Detection

The fluorescence polarization—template-directed dye-terminator incorporation (FP-TDI) SNP assay (Chen et al. 1999) uses single nucleotide polymerase extension with allele-specific fluorescence-labeled dideoxynucleotide terminators. The genotypes of the extension products are characterized by monitoring the unique change in fluorescence polarization. The FP-TDI approach offers a simple SNP detection method but with a limited scope of multiplexing.

The BEAMing (beads, emulsion, amplification, and magnetics) approach (Dressman et al. 2003) has been developed for detecting genetic variations with the aim of high-sensitivity and high-throughput. In this method, each individual DNA template is discretely amplified by a large number of oligonucleotide primers that are immobilized on a magnetic bead in a water-oil emulsion, the target SNPs are distinguished by unique fluorescent dye-labeled probes and characterized using flow cytometry. The BEAMing approach not only allows the identification of allelic variations, but also offers the ability to quantify these variations. In addition, the DNA sample can be recovered from the flow cytometer for further analysis. The disadvantage of the BEAMing method is that multiple steps of manipulation are required, which can lead to difficulties in accurate characterization of allele frequency.

Tong et al. have developed a multiplex fluorescent SNP assay using SBE and combinatorial fluorescence energy transfer (CFET) tags (Tong et al. 2002). A larger number of CFET tags with unique fluorescence signatures have been constructed using a small number of fluorophores with distinct emissions by exploiting fluorescence energy transfer and the combinatorial concept. The CFET tags can all be excited at a single wavelength of 488 nm and detected and differentiated by a simple optical system. The principle of the approach is outlined as follows. A library of CFET-labeled oligonucleotide primers are designed and synthesized so that the nucleotide at the 3'-end is complementary to a particular SNP in the template. In a single tube reaction, the CFET-labeled oligonucleotide primers and biotin-ddNTPs are used to perform SBE on the DNA templates containing the SNPs. CFET-labeled primer that perfectly matches with the DNA template is extended with a biotin-ddNTP by DNA polymerase with. The 3'-biotinylated DNA products are isolated by capture with streptavidin-coated magnetic beads, while the unextended primers and other components in the reaction are not captured and eliminated by washing. A multicolor laser-induced fluorescence electrophoresis instrument is used to analyze the biotinylated fluorescent DNA products. The SNPs are determined by the distinct fluorescence signature and electrophoretic mobility of each DNA extension product in the electropherogram. Using oligonucleotide ligation, Tong et al. (2001) have used CFET tags to detect multiplex nucleotide variations simultaneously from the retinoblastoma tumor suppressor gene.

Figure 3:
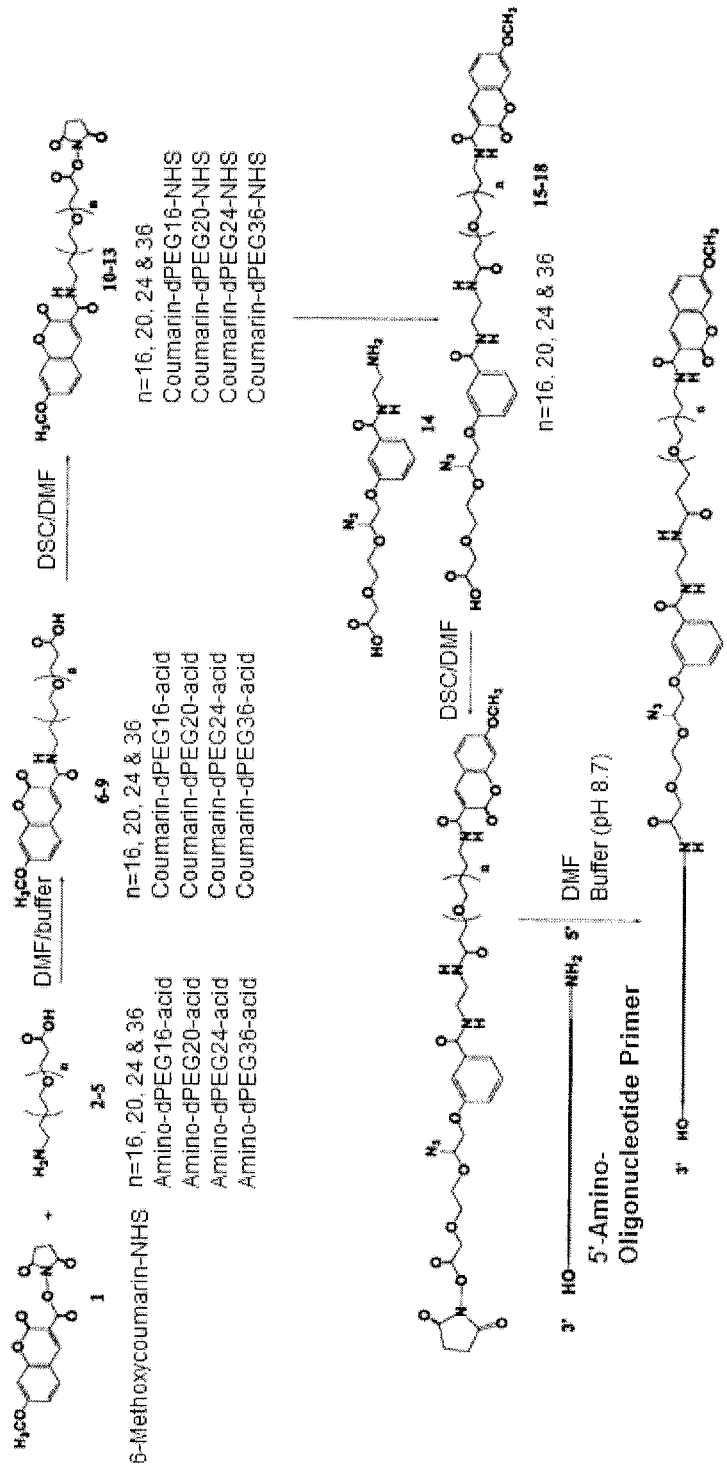
FIG. 3. Scheme for the design and synthesis of the cleavable PEG-labeled primers.

To demonstrate the feasibility of the SM-EMS assay, four polymers (PEG16, PEG20, PEG24 and PEG36) were selected to label four primers based on the sequences of the retinoblastoma 1 tumor suppressor gene. The synthesis scheme for the cleavable PEG labeled primers is shown in FIG. 3, and the steps are identified below with the numbers used to label them in FIG. 3. The commercially available Amino-dPEG-acids (2-5) were first reacted with 6-methoxy coumarin-NHS ester (1) to provide the corresponding coumarin-(PEG)n-acids (6-9), which were converted to the corresponding NHS esters (10-13) by reacting them with disuccinimidyl carbonate (DSC) and triethylamine in anhydrous DMF. The resulting four different coumarin-(PEG)n-NHS esters (10-13) were then reacted with azido-linker (14) (Guo et al. 2008) to yield the corresponding coumarin-(PEG)n-azido-acids (15-18), which were subsequently converted to NHS esters. Coupling of the resulting NHS esters of the azido-linker PEGs with the 5'-amino-primer yielded the target cleavable PEG labeled primers (PEG-primers).

EXPERIMENT 1

Synthesis of Primers Coupled with Cleavable Coumarin-(PEG)$_n$ Analogs

All of the PEG analogs were purified by reverse-phase HPLC on a 250×10 mm column (Supelco), using the following mobile phases: A, 8.6 mM Et$_3$N/100 mM 1,1,1,3,3,3-hexafluoro-2-propanol in water (pH 8.1) and B, methanol; or A, 0.1M triethylammonium acetate (pH 7.5) buffer and B, acetonitrile gradient. The mass spectra for the corresponding molecules were obtained on a MALDI-TOF MS spectrometer (Voyager-DE BioSpectrometry Workstation, PerSeptiveBiosystems). All steps of the synthetic scheme are shown in FIG. 3, and are identified below with the numbers used to label them in FIG. 3.

(A) Synthesis of Coumarin-PEG-Acids and NHS Esters

The commercially available Amino-PEG-acids (Amino-dPEG$_{16, 20, 21, 36}$-acids) (2-5) were first reacted with 6-methoxy coumarin-NHS ester (1) to produce the corresponding coumarin-(PEG)$_n$-acid (6-9). Thus, to amino-(PEG)$_n$-acid (2-5, 1 eq) dissolved in carbonate-bicarbonate buffer (pH 8.6), coumarin-NHS (1, 1.5 eq) in DMF was added, and the reaction mixture was stirred overnight. The coumarin-(PEG)$_n$-acids (6-9) were purified by silica-gel chromatography using a $CH_2Cl_2$-MeOH (5-15%) mixture and the appropriate fractions were combined. The purified compounds were analyzed by $^1$H NMR and MALDI-TOF MS. The MALDI-TOF MS data for these molecules are listed as follows: Coumarin-PEG16-COOH (6) [Expected molecular weight (EMW)=996 Da; Observed molecular weight (OME)=1016 Da)]; Coumarin-PEG20-COOH (7) (EMW=1172 Da; OME=1192 Da); Coumarin-PEG24-COOH (8) (EMW=1348 Da; OME=1368 Da); Coumarin-PEG36-COOH (9) (EMW=1877 Da; OME=1899 Da). The difference between the OME and EMW is due to presence of one sodium ion ($Na^+$) in the coumarin-(PEG)$_n$-acids. The coumarin-(PEG)$_n$-acids were converted to the corresponding NHS esters (10-13) by reacting with 1.5 eq. of disuccinimidyl carbonate (DSC) and 2 eq of triethylamine in anhydrous DMF for 2 hours. The NHS ester, which moves slightly faster than the acid on silica-gel plates, was purified by silica-gel chromatography using a $CH_2Cl_2$-MeOH (5-15%) mixture and used in the next step.

(B) Synthesis of the Coumarin-(PEG)$_n$-Azido-Acids (15-18) Using Azido-Based Linker Synthesis of (2-{2-[3-(2-amino-ethylcarbamoyl)-phenoxy]-1-azido-ethoxy}-ethoxyl)-acetic acid (14, FIG. 6) was carried out according to the literature procedure[64]. This azido-linker was reacted with four different coumarin-(PEG)$_n$-NHS esters (10-13) to provide the corresponding coumarin-(PEG)$_n$-azido-acids (15-18) (FIG. 3), which were purified by HPLC and characterized by MALDI-TOF MS. The MALDI-TOF MS data for these molecules are listed as follows: Coumarin-PEG16-N3-Linker-COOH (15) [Expected molecular weight (EMW)=1345 Da; Observed molecular weight (OME)=1346 Da)]; Coumarin-PEG20-N$_3$-Linker-COOH (16) (EMW=1521 Da; OME=1521 Da); Coumarin-PEG24-N$_3$-Linker-COOH (17) (EMW=1698 Da; OME=1699 Da); Coumarin-PEG36-N$_3$-Linker-COOH (18) (EMW=2226 Da; OME=2230 Da).

(C) Coupling of 5'-Amino-Primers with Coumarin-(PEG)$_n$-Azidolinker-Acids

To a solution of Coumarin-(PEG)$_n$-azidolinker-acid (15-18) (3.14 mmol) dissolved in anhydrous DMF (300 ml) was added a solution of 0-(N-succinimidyl)-1,1,3,3-tetramethyluronium tetrafluoroborate (TSTU, 3 mg, 10 mmol) in anhydrous DMF (100 ml). The reaction mixture was stirred under an argon atmosphere at room temperature for 1 hour to produce the corresponding NHS esters for coupling with the 5'-amino-primers (Primer-1, 5'-NH$_2$-CAGATGATATGTTCTAATTC-3' (SEQ ID NO:1); Primer-2, 5'-NH$_2$-PEG20-TCACAAAGTGTATTTAGCCG-3' (SEQ ID NO:2); Primer-3, 5'-NH$_2$-CAGATGATATGTTCTAATTA-3' (SEQ ID NO:3); Primer-4, 5'-NH$_2$-GAGATAGGCTAGC-CGATACA-3' (SEQ ID NO:4)). The appropriate 5'-amino-primer (250 nmol) in 0.1 M $NaHCO_3$—$Na_2CO_3$ buffer (pH 8.7, 250 ml) was added to the NHS ester of the Coumarin-(PEG)$_n$-azidolinker-acid and the reaction mixture was stirred at room temperature overnight to yield the target molecules, the cleavable PEG-primers (FIG. 3), which were purified by reverse-phase HPLC and characterized by MALDI-TOF MS. The MALDI-TOF MS data for the PEG-primers are listed as follows: Coumarin-PEG16-N$_3$-Linker-Primer-1 (PEG16-Primer-1) [Expected molecular weight (EMW)=7612 Da; Observed molecular weight (OME)=7630 Da)]; Coumarin-PEG20-N$_3$-Linker-Primer-2 (PEG20-Primer-2)(EMW=7798 Da; OME=7797 Da); Coumarin-PEG24-N$_3$-Linker-Primer-3 (PEG24-Primer-3) (EMW=7989 Da; OME=7989 Da); Coumarin-PEG36-N$_3$-Linker-Primer-4 (PEG36-Primer-4) (EMW=8562 Da; OME=8550 Da).

EXPERIMENT 2

Figure 4:
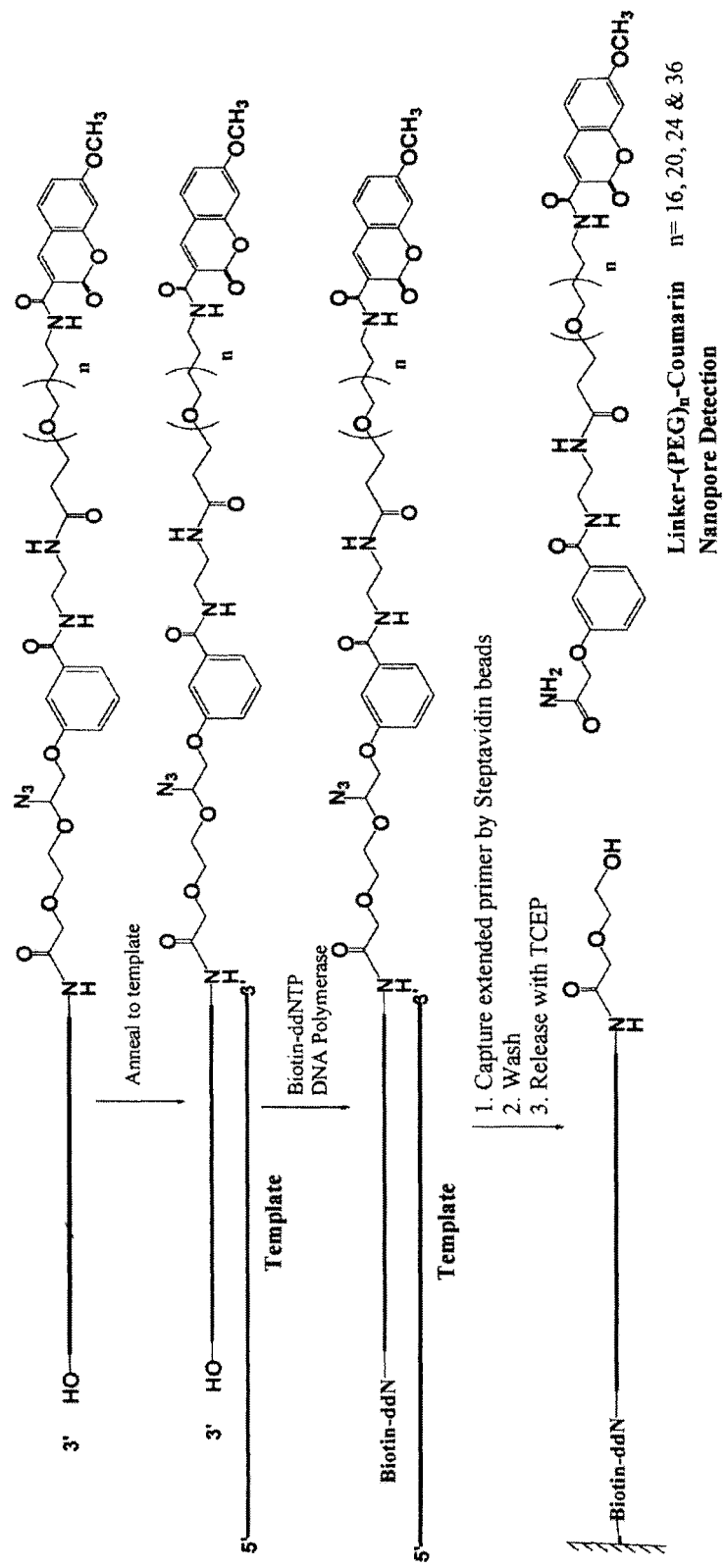
FIG. 4. Molecular mechanism of the SM-EMS assay with PEG-Primers and biotin-ddNTPs (B-ddNTP). The perfectly complementary, cleavably PEG-labeled primer targeting a specific SNP in the DNA template is extended by polymerase with a B-ddNTP. The streptavidin-coated magnetic beads only capture the biotinylated DNA extension products while the other components are washed away. Treatment of the captured DNA products with TCEP cleaves the PEGs [Linker-(PEG)n-Coumarin], which are analyzed by nanopore to yield unique electrical current blockade signatures for SNP characterization.

Characterization of the Cleavable PEG-Labeled Primers and their SBE Cleavage Products FIG. 4 outlines the molecular mechanism of the SM-EMS assay with PEG-primers and biotin-ddNTPs. The DNA template containing polymorphic sites is incubated with a library of PEG-primers, Biotin-ddNTPs and DNA polymerase. The nucleotide at the 3'-end of each PEG-labeled primer is complementary to a particular SNP in the DNA template. Only the perfectly complementary PEG-labeled primer is extended by DNA polymerase with a Biotin-ddNTP. The streptavidin-coated magnetic beads only capture the biotinylated DNA extension products while the other components are washed away. Treatment of the captured DNA products with TCEP cleaves the PEGs, which will be analyzed by nanopore for their unique electrical current blockade signatures, each of which determines a unique SNP.

Figure 5:
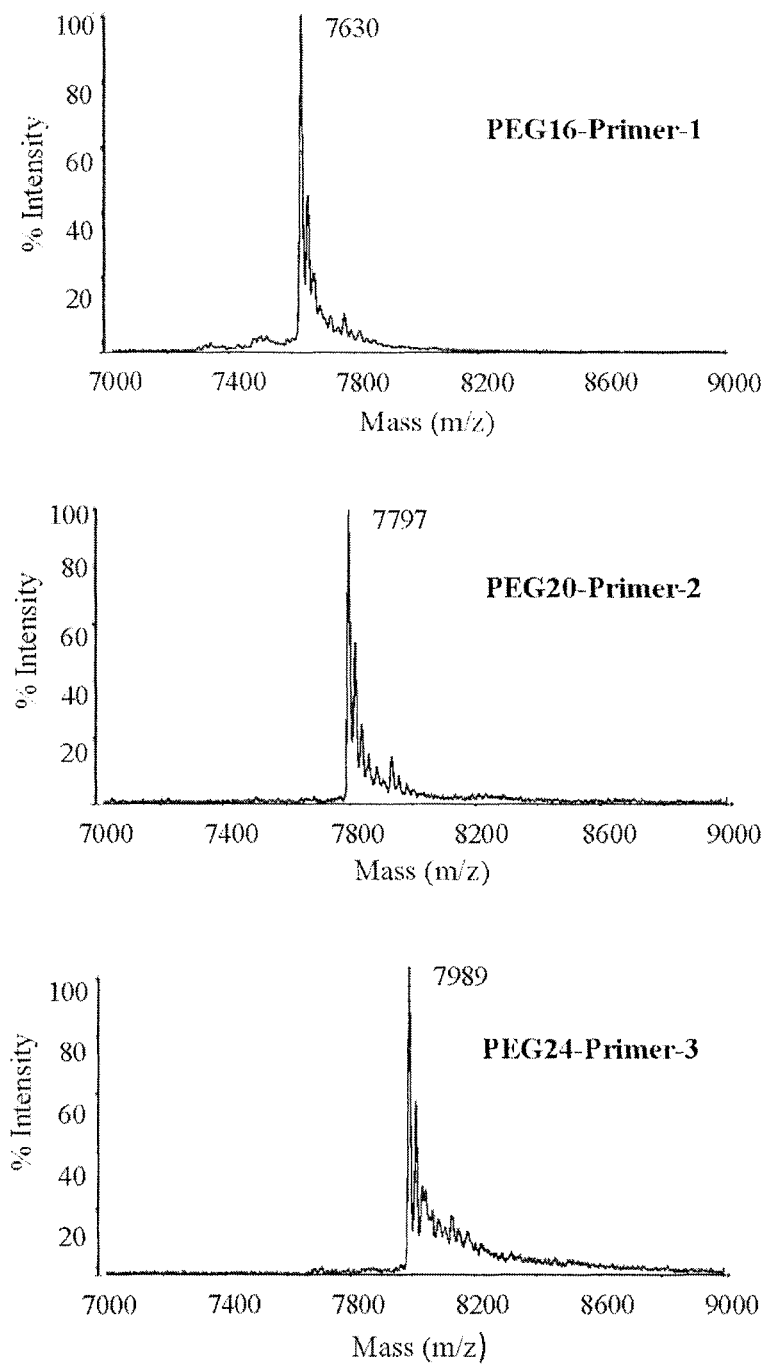
FIG. 5. MALDI-TOF mass spectra of 3 PEG-labeled primers: PEG16-Primer-1, PEG20-Primer-2, and PEG24-Primer-3. The mass values on the spectra match perfectly with the corresponding PEG-labeled primers.
Figure 6:
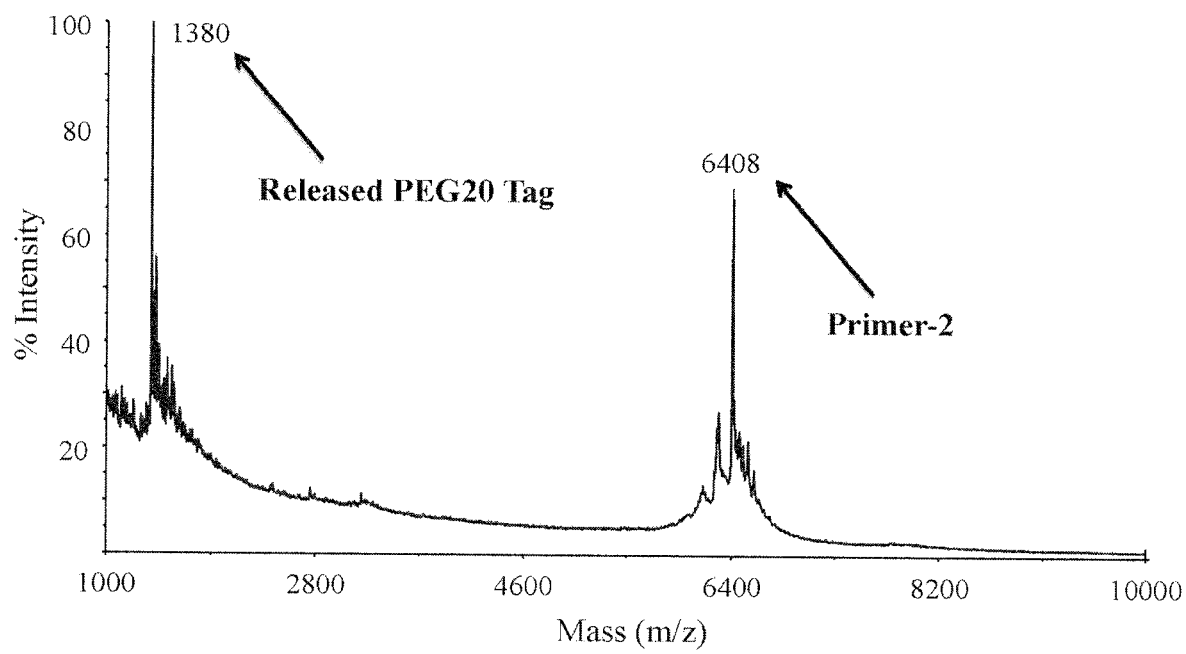
FIG. 6. MALDI-TOF mass spectrum shows that TCEP completely cleaves the azido-based linker in PEG20-Primer-2 leading to the released PEG20 tag and Primer-2. PEG20 tag: m/z=1380 Da; Primer-2: m/z=6408 Da.
Figure 7:
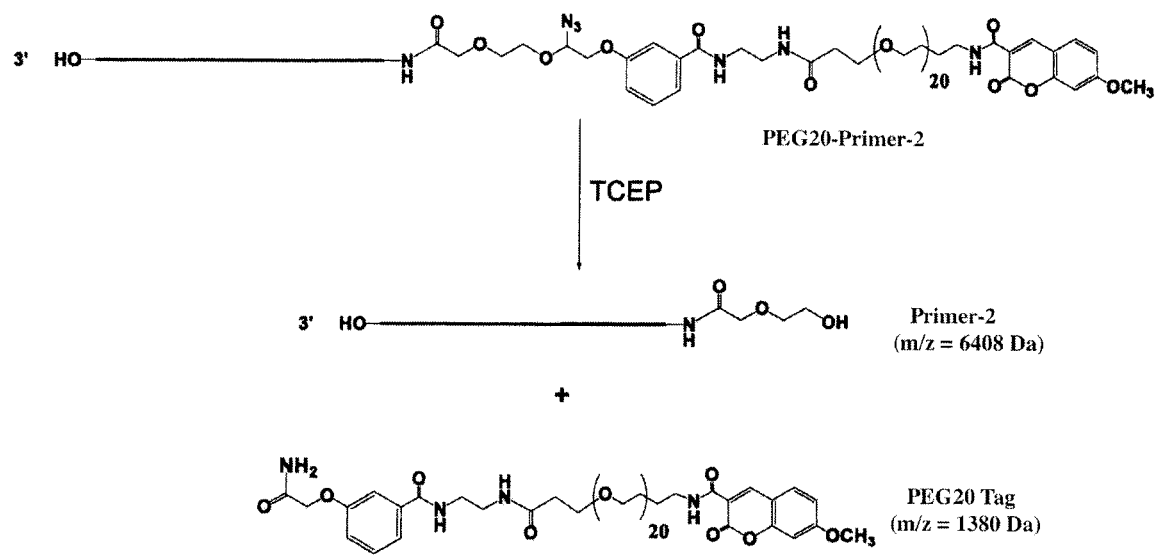
FIG. 7. The cleavage reaction scheme for PEG20-Primer-2 by TCEP. Treatment of PEG20-Primer-2 by TCEP completely cleaves the azido-based linker leading to the released PEG20 tag and Primer-2.

Three PEG-primers were characterized by MALDI-TOF MS and the results are shown in FIG. 5. Each PEG-primer produces a single peak in the mass spectrum with molecular weights of 7630 Da for PEG16-Primer-1, 7797 Da for PEG20-Primer-2, and 7989 Da for PEG24-Primer-3, confirming that each PEG-primer is pure with the expected sequences and PEG label. Next, the PEG cleavage efficiency by TCEP from the PEG-primer was evaluated. PEG20-Primer-2 was first treated with TCEP for 25 minutes and the resulting products were analyzed by MALDI-TOF MS. As shown in FIG. 6, two clean peaks were produced in the mass spectra: the peak with a molecular weight of 1380 Da is from the cleaved PEG20 tag; the peak with a molecular weight of 6408 Da is from the primer-2 with the PEG20 tag cleaved. There is no peak for the parent PEG20-Primer-2, indicating that the TCEP cleavage efficiency is 100%. The cleavage reaction scheme for PEG20-Primer-2 by TCEP is shown in FIG. 7.

Figure 8:
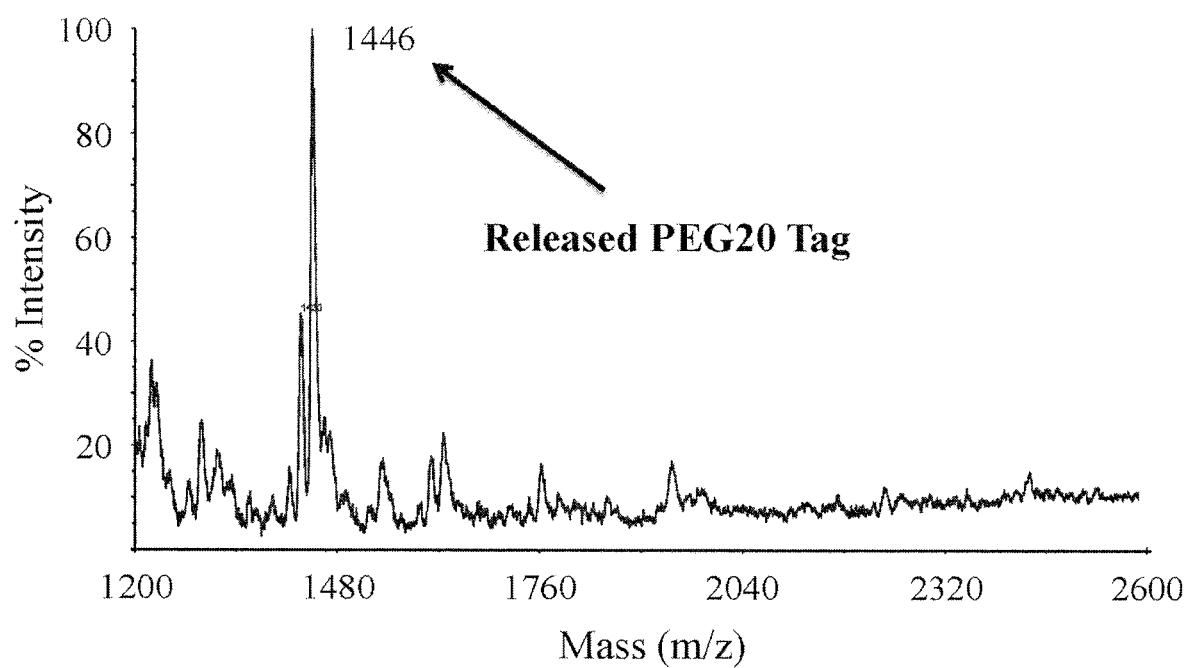
FIG. 8. MALDI-TOF mass spectrum of the released PEG20 tag. An extension reaction was performed with PEG20-Primer-2 and Biotin-aha-dUTP and the products were captured with streptavidin magnetic beads. TCEP treatment of the captured DNA products led to the release of the PEG20 tag (m/z=1446 Da; PEG20+2Na$^+$).

To establish the feasibility of the SM-EMS assay at the molecular level, PEG20-Primer-2 was used to perform all the steps according to the scheme shown in FIG. 1 except that the final cleaved PEG20 tag was detected by MALDI-TOF MS instead of nanopore. The aim here was to validate the procedures for the key steps of the SM-EMS assay. If MALDI-TOF MS analysis of the cleaved product from the streptavidin-coated magnetic beads matches the expected PEG20 tag, the nanopore characterization of the released PEG20 tag should be readily accomplished according to the established procedure in the literature (Kumar et al. 2012). A synthetic DNA template with a nucleotide "A" immediately after the priming site of the PEG20-Primer-2 and biotin-dUTP is used to perform the SBE reaction. After the polymerase extension reaction, the products are captured on the streptavidin-coated magnetic beads. Only the DNA product carrying a biotin at the 3'-end and a PEG20 at the 5'-end is captured, while the other components of the reaction are washed away. The DNA product captured on the streptavidin-coated magnetic beads is then treated with TCEP, and the cleaved product is collected and measured by MALDI-TOF MS. A single peak with a molecular weight of 1446 Da is shown in FIG. 8, which matches the mass of the cleaved PEG20 tag carrying 2 sodium ions (PEG20+2Na$^+$).

(A) MALDI-TOF MS Measurement of PEG-Primers

PEG-Primers (~20 pmol) (PEG16-Primer-1: 5'-PEG16-CAGATGATATGTTCTAA-TTC-3' (SEQ ID NO:1); PEG20-Primer-2: 5"-PEG20-TCACAAAGTGTATT-TAGCCG-3' (SEQ ID NO:2) and PEG24-Primer-3: 5'-PEG24-CAGATGATATGTTCTAATTA-3' (SEQ ID NO:3)) were used to obtain the mass spectra shown in FIG. 5.

(B) TCEP Treatment of PEG20-Primer-2 to Cleave the Azido-Based Linker Yielding the PEG20 Tag Treatment of PEG20-Primer-2 (200 pmol) with 10 µl of TCEP (50 mM) for 25 minutes at 65° C. produced the released PEG20 tag and the primer-2 with the PEG20 tag removed. Both products were desalted through a ZipTip 018 (ZTC18S096, Millipore) and analyzed by MALDI-TOF MS, and the results are shown in FIG. 6.

(C) PEG-Primer Extension with Biotin-Aha-dUTP

Biotin-aha-dUTP (Cat # B32766, Life Technologies) was used for the polymerase extension reaction with PEG20-Primer-2 (5'-PEG20-TCACAAAGTGTATTTAGCCG-3') (SEQ ID NO:2) and the DNA template (5'-TAGCCTATC-TACGGCTAAATACACTTTGTGAACGCCTTCTG-3' (SEQ ID NO: 8)), based on the sequence of the retinoblastoma 1 tumor suppressor gene. Thermo Sequenase (4 U/reaction) was used in a total reaction volume of 20 µl with 100 pmol primer, 60 pmol template and 300 pmol biotin-aha-dUTP. The extension was performed using the following cycle protocol: (93° C./30", 55° C./30", 72° C./1')×20, 93° C./2', and then stored at 4° C.

(D) Capture of DNA Extension Product with Streptavidin Magnetic Beads and TCEP Treatment to Release the PEG20 Tag One hundred microliters of streptavidin-coated magnetic beads (DynabeadsMyOne Streptavidin C1, Invitrogen) were washed twice with 1× binding and washing (B&W) buffer (10 mM Tris-HCl, 1 mM EDTA, 2.0 M NaCl, pH 7.5) and then resuspended in 50 µl of 2×B&W buffer. An equal volume of primer extension products obtained with PEG20-Primer-2 and Biotin-aha-dUTP was added to the 2×B&W buffer. The mixture was placed on a rotator for 15 minutes at room temperature. The supernatant was removed while the magnetic beads were immobilized with a magnet. The beads were then washed three times with 100 µl of 1× B&W buffer and then immobilized with a magnet. 100 µl of TCEP (50 mM) was added to resuspend the beads and incubation carried out at 65° C. for 25 min. The resulting TCEP solution containing the released PEG20 tag was desalted using a ZipTip C18 (ZTC18S096, Millipore) and analyzed by MALDI-TOF MS, and the result is shown in FIG. 8.

EXPERIMENT 3

Identifying Gene Targets Via Primers Having MassTags Attached

Figure 9:
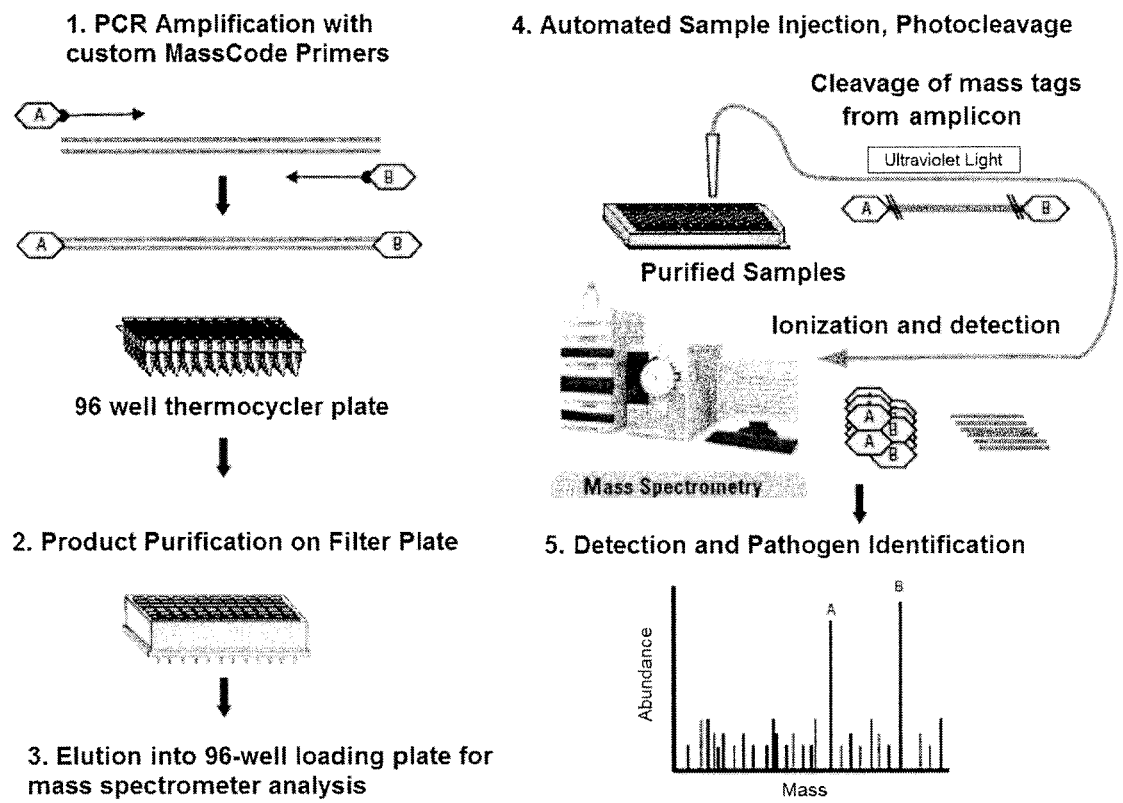
FIG. 9. Scheme for MassTag PCR.

PCR using custom MassCode primers (primers with MassTags attached) has been used to identify gene targets (Briese et al. 2005 and Palacios et al. 2006). A library of primers is prepared, each with a unique MassTag attached via a cleavable linker. PCR amplification is performed on the target gene, so that the two primers complementary to each strand of the target gene are incorporated to the PCR products. The PCR products undergo a purification step, so as to remove the unreacted excess primers. These PCR products are then eluted into a multi-well plate for mass spectrometry analysis. The two mass tags are cleaved and analyzed with a mass spectrometer, identifying the two cognate tags, therefore identifying the primers from the library to which they were originally attached. This information is used to identify the target gene. This process requires the use of bulky and expensive mass spectrometry equipment, however (See FIG. 9).

Identifying Gene Targets Via Primers Having NanoTags Attached

Figure 10:
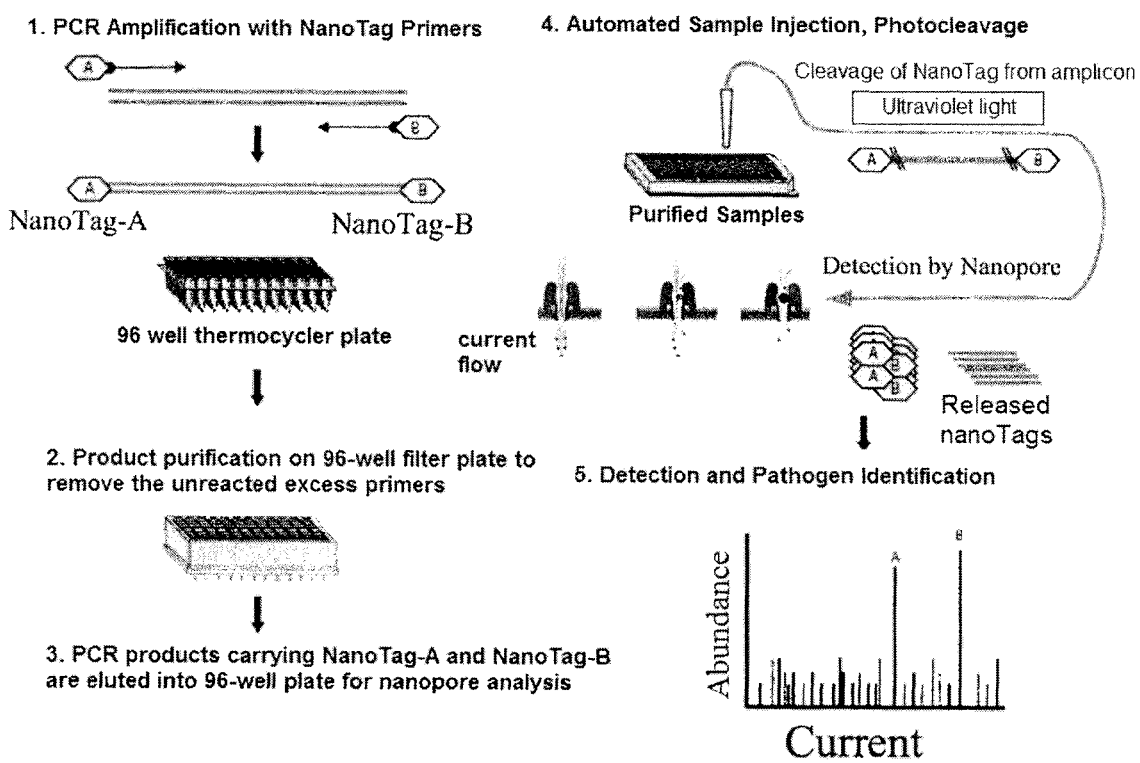
FIG. 10. Scheme for NanoTag PCR.

PCR using custom NanoTag primers (primers with NanoTags attached) uses a process related to that using MassTag primers, described hereinabove, but without the drawback of having to use a bulky and expensive mass spectrometer. A library of primers is prepared, each with a unique NanoTag attached via a cleavable linker. PCR amplification is performed on the target gene, so that the two primers complementary to the target gene are incorporated to the PCR products. The PCR products undergo a purification step, so as to remove the unreacted excess primers. These PCR products are then eluted into a multi-well plate for nanopore analysis. The two NanoTags are cleaved and analyzed with a nanopore, identifying the two cognate tags, thereby identifying the primers from the library to which they were originally attached. This information is used to identify the target gene (see FIG. 10).

EXPERIMENT 4

Quantitative PCR with Fluorescence Detection

Figure 11:
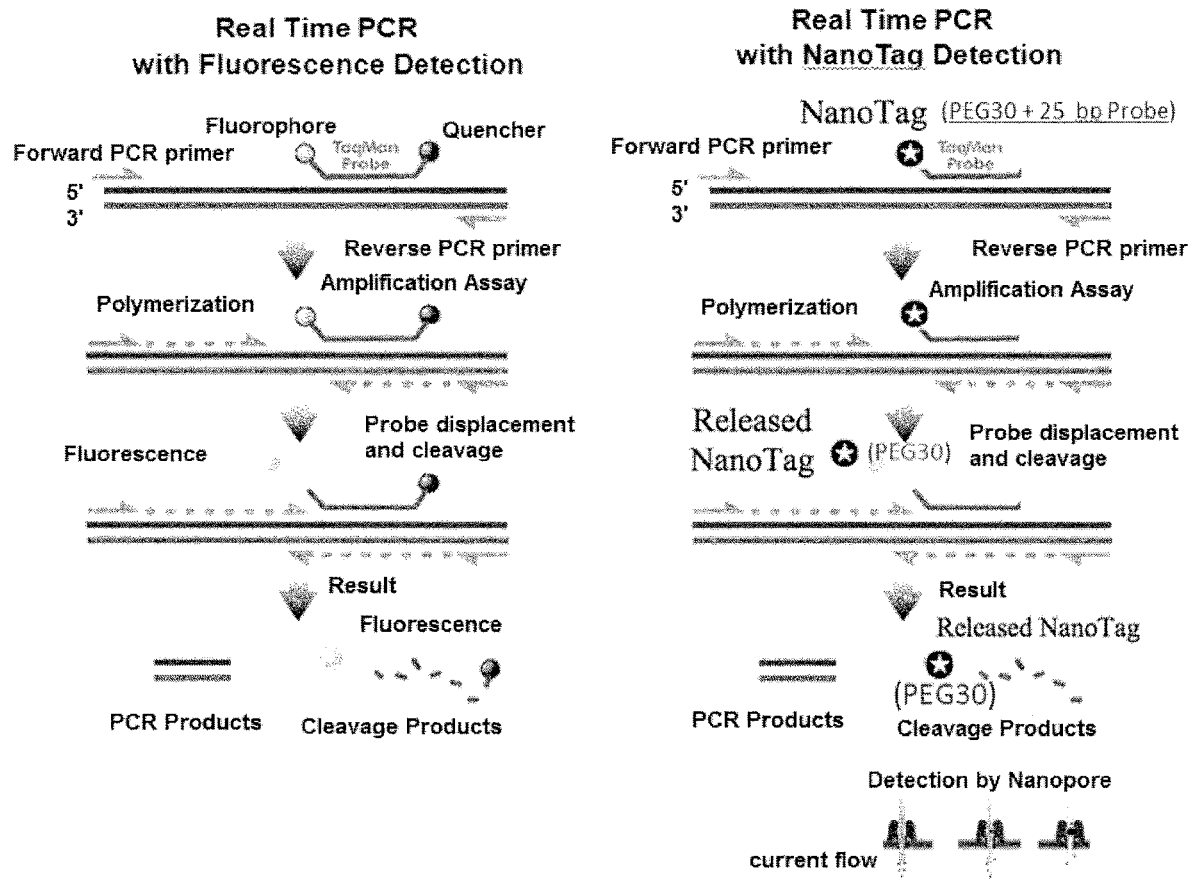
FIG. 11. Scheme for real-time quantitative PCR, using fluorescence detection (left side) and NanoTag detection (right side).

In real-time quantitative PCR with fluorescence detection, a TaqMan probe partially hybridizes to the target molecule. Each end of the probe typically has a stretch of nucleotides that does not hybridize to the target molecule. This probe has attached a fluorophore and a quencher, so that the fluorophore does not exhibit fluorescence when attached to the probe. The fluorophore is attached to the probe, typically at the 5'-terminus of the probe, and the quencher is typically attached to the 3'-terminus of the probe. During PCR, the 5'-3' exonuclease activity of Taq polymerase causes the release of the fluorophore from the dual-labeled probe. Upon release, the fluorophore is free from the influence of the quencher, and fluoresces (See FIG. 11, left side). Assuming the introduction of sufficient probe, the level of fluorescence will increase as the amount of target DNA increases.

Quantitative PCR with NanoTag Detection

Real-time quantitative PCR analysis with NanoTag detection offers the benefits of the same analysis with fluorophore detection, but with the added benefits of using nanopore detection, as described hereinabove. When performing real-time quantitative PCR analysis with NanoTag detection, as opposed to fluorescence detection, the probe only has one label, which can be detected by a nanopore, attached at the 5' terminal of the probe. No quencher is required. Typically, the probe comprises a 5'-terminal tail which does not hybridize to the target molecule. During PCR, the exonuclease activity of the Taq polymerase causes the NanoTag to be released, followed by detection by a nanopore to identify the target. The greater the electronic signal detected by the nanopore, the more NanoTag was released (See FIG. 11, right side). An increase in NanoTag release correlates to a greater abundance of the target.

CONCLUSION

A novel approach for electronic multiplex SNP assay using a library of oligonucleotide primers labeled with PEG polymers of different length through an azido-based linker using nanopore detection with single molecule sensitivity is proposed. The feasibility of this approach at the molecular level has been established. The investigations included the design and synthesis of the novel cleavable PEG labeled primers and their characterization by MALDI-TOF MS. The azido-based cleavable linker was shown to be stable during the polymerase reaction and the solid phase capture. Treatment of the PEG labeled DNA products captured on the solid phase with TCEP led to quantitative cleavage of the azido-based linker to release the expected PEG tag, the structure of which was confirmed by MALDI-TOF MS. The characterization of the PEG tag by nanopore can be easily performed using established procedures in the future (Robertson et al. 2007 and Kumar et al. 2012).

PEGs of different sizes have been shown to be electronically detected and differentiated and at single molecule level by a protein nanopore. Each of the different sized PEGs produces a unique electrical current blockade signature in the nanopore. Based on previous results, it is expected that up to 20 PEGs of different sizes can be used to develop the single molecule electronic multiplex SNP assay. Thus, a library of 20 oligonucleotide primers corresponding to different SNP sites of a target gene can be labeled with the 20 PEGs through the azido-based linker that can be efficiently cleaved by TCEP. Since the nucleotide at the 3'-end of each PEG-labeled oligonucleotide primer is complementary to a particular SNP in the template, these PEG-labeled primers can be used with biotinylated dideoxynucleotides (biotin-ddNTPs) for single base extension in a single tube. Only the PEG-labeled primer that is fully complementary to the DNA template will be extended by DNA polymerase with a biotin-ddNTP. The PEG-labeled DNA extension products that carry a biotin at the 3'-end will be captured with streptavidin-coated magnetic beads; the unextended PEG-labeled primers and other components of the SBE reaction will be eliminated by washing. Treatment of the captured DNA products with TCEP cleaves the PEGs, which will be analyzed by nanopore. Each different-sized PEG will produce a unique nanopore electrical current blockade signature at single molecule level, which will lead to the identification of multiplex SNPs.

There are extensive ongoing efforts to construct nanopore arrays for high-throughput biomolecular analyses (dela Torre et al. 2012 and Yang et al. 2013). Thus, the single molecule electronic multiplex SNP assay described herein can be readily used in the nanopore-array to form a high-throughput, cost effective genetic variation analysis system with high-sensitivity at the single molecule level. The combination of the following advances makes this approach feasible: (1) the established organic synthesis method to create the new cleavable PEG-labeled primers; (2) the molecular affinity between biotin and streptavidin; (3) the specificity of DNA polymerase in SBE; (4) site specific cleavage with TCEP without damaging DNA; and (5) the ability of the nanopore to serve as an single molecule electronic detector.

Further efforts in the future for fully developing the proposed single molecule electronic multiplex SNP assay will include design and synthesis of a large library of the cleavable PEG-primers and performance of all the steps outlined in FIG. 1 for high-level multiplex SNP characterization by nanopores.

REFERENCES

Bai, R. K. & Wong, L. J. Detection and quantification of heteroplasmic mutant mitochondrial DNA by real-time amplification refractory mutation system quantitative PCR analysis: a single-step approach. *Clin. Chem.* 50, 996-1001 (2004).

Bardelli, A. et al. Mutational analysis of the tyrosine kinome in colorectal cancers. *Science* 300, 949 (2003).

Bentley, D. R. et al. Accurate whole human genome sequencing using reversible terminator chemistry. *Nature* 456, 53-59 (2008).

Bezrukov, S. M. et al. Dynamics and free energy of polymers partitioning into a nanoscale pore. *Macromolecules* 29, 8517-22 (1996).

Briese T. et al. Diagnostic system for rapid and sensitive differential detection of pathogens. *Emerg Infect Dis.* 11(2):310-13 (2005).

Cerezo, M. et al. Applications of MALDI-TOF MS to large-scale human mtDNA population-based studies. *Electrophoresis* 30, 3665-3673 (2009).

Chen, X. et al. Fluorescence polarization in homogeneous nucleic acid analysis. *Genome Res.* 9: 492-498 (1999).

Cherf, G. M. et al. Automated forward and reverse ratcheting of DNA in a nanopore at 5-Å precision. *Nat. Biotechnol.* 30, 344-348 (2012).

Chowdhury, J. et al. Microfluidic Platform for Single Nucleotide Polymorphism Genotyping of the Thiopurine S-Methyltransferase Gene to Evaluate Risk for Adverse Drug Events. *J. Mol. Diagn.* 9, 521-529 (2007).

Clarke, J. et al. Continuous base identification for single-molecule nanopore DNA sequencing. *Nat. Nanotechnol.* 4, 265-70 (2009).

dela Torre, R. et al. Fabrication and characterization of solid-state nanopore arrays for high-throughput DNA sequencing. *Nanotechnology* 23, 385308 (2012).

Ding, C. & Cantor, C. R. A high-throughput gene expression analysis technique using competitive PCR and matrix-assisted laser desorption ionization time-of-flight MS *Proc. Natl. Acad. Sci. USA,* 100, 3059-3064 (2003).

Ding, C. & Cantor, C. R. Direct molecular haplotyping of long-range genomic DNA with M1-PCR. MS *Proc. Natl. Acad. Sci. USA,* 100, 7449-7453 (2003).

Dressman, D. et al. Transforming single DNA molecules into fluorescent magnetic particles for detection and enumeration of genetic variation. *Proc. Natl. Acad. USA* 100, 8817-8822 (2003).

Eid, J. et al. Real-Time DNA Sequencing from Single Polymerase Molecules. *Science* 323, 133-138 (2009).

Fei, Z. et al. MALDI-TOF mass spectrometric typing of single nucleotide polymorphisms with mass-tagged ddNTPs. *Nucleic Acids Res.,* 26, 2827-2828 (1998).

Frazer, K. A. et al. A second generation human haplotype map of over 3.1 million SNPs. *Nature* 449, 851-861 (2007).

Griffin, T. J. et al. Direct genetic analysis by matrix-assisted laser desorption/ionization mass spectrometry. *Proc. Natl. Acad. Sci. USA* 96, 6301-6306 (1999).

Griffin, T. J. & Smith, L. M. Single-nucleotide polymorphism analysis by MALDI-TOF mass spectrometry. *Trends. Biotechnol.* 18, 77-84 (2000).

Guo, J. et al. Four-color DNA sequencing with 3-O-modified nucleotide reversible terminators and chemically cleavable fluorescent dideoxynucleotides. *Proc. Natl. Acad. Sci. USA* 105, 9145-9150 (2008).

Haff, L. A. & Smirnov, I. P. Multiplex genotyping of PCR products with mass tag-labeled primers. *Nucleic Acids Res.,* 25, 3749-3750 (1997).

Hardenbol, P. et al. Multiplexed genotyping with sequence-tagged molecular inversion probes. *Nat. Biotechnol.* 21: 673-678 (2003).

Harris, T. D. et al. Single-Molecule DNA Sequencing of a Viral Genome. *Science* 320, 106-109 (2008).

Hartmann, A. et al. Validation of microarray-based resequencing of 93 worldwide mitochondrial genomes. *Hum. Mutat.* 30, 115-122 (2009).

Hollstein, M. et al. p53 mutations in human cancers. *Science.* 253, 49-53 (1991).

Ju, J. et al. Energy transfer fluorescent dye-labeled primers for DNA sequencing and analysis. *Proc. Natl. Acad. Sci. USA* 92, 4347-4351 (1995).

Ju, J. et al. Cassette labeling for facile construction of energy transfer fluorescent primers. *Nucleic Acids Res.* 24, 1144-1148 (1996).

Ju, J. et al. Four-Color DNA Sequencing by Synthesis Using Cleavable Fluorescent Nucleotide Reversible Terminators. *Proc. Natl. Acad. Sci. USA* 103, 19635-19640 (2006).

Kasianowicz, J. J. & Bezrukov, S. M. Protonation dynamics of the alpha-toxin ion channel from spectral analysis of pH-dependent current fluctuations. *Biophys. J.* 69, 94-105 (1995).

Kasianowicz, J. J. et al. Characterization of individual polynucleotide molecules using a membrane channel. *Proc Natl Acad Sci USA* 93, 13770-13773 (1996).

Kasianowicz, J. J. et al. Physics of DNA threading through a nanometer pore and applications to simultaneous multianalyte sensing. In *Structure and Dynamics of Confined Polymers*, ed. Kasianowicz, J. J., Kellemayer, M. S. Z. & Deamer, D. W., NATO Science Series, Kluwer Academic Publishers, The Netherlands 87, 141-164 (2002).

Kasianowicz, J. J. et al. Nanoscopic porous sensors. *Annu Rev Anal Chem* 1, 737-766 (2008).

Kheterpal, I. et al. DNA Sequencing Using a Four-Color Confocal Fluorescence Capillary Array Scanner. *Electrophoresis* 17, 1852-1859 (1996).

Kim, S. et al. Solid phase capturable dideoxynucleotides for multiplex genotyping using mass spectrometry. *Nucleic Acids Res.* 30, e85 (p 1-6) (2002).

Kim, S. et al. Multiplex Genotyping of the Human β2-Adrenergic Receptor Gene Using Solid Phase Capturable Dideoxynucleotides and Mass Spectrometry. *Analytical Biochemistry* 316, 251-258 (2003).

Kim, S. et al. Thirty fold multiplex genotyping of the p53 gene using solid phase capturable dideoxynucleotides and mass spectrometry. *Genomics* 83, 924-931 (2004).

Krasilnikov, 0. V. Sizing channels with neutral polymers. In *Structure and Dynamics of Confined Polymers*, ed. Kasianowicz, J. J., Kellemayer, M. S. Z. & Deamer, D. W. NATO Science Series, Kluwer Academic Publishers, The Netherlands 87, 97-116 (2002).

Kumar, S. et al. PEG-labeled nucleotides and nanopore detection for single molecule DNA sequencing by synthesis. *Sci Rep.* 2, 684, 1-8 (2012).

Kwok, P. Y. High-throughput genotyping assay approaches. *Pharmacogenomics* 1, 95-100 (2000).

Lander, E. S. et al. Initial sequencing and analysis of the human genome. *Nature* 409, 860-921 (2001).

Lyamichev, V. et al. Polymorphism identification and quantitative detection of genomic DNA by invasive cleavage of oligonucleotide probes. *Nat. Biotechnol.* 17, 292-296 (1999).

Manrao, E. A. et al. Reading DNA at single-nucleotide resolution with a mutant MspA nanopore and phi29 DNA polymerase. *Nat. Biotechnol.* 30, 349-353 (2012).

Margulies, M. et al. Genome sequencing in microfabricated high-density picolitre reactors. *Nature* 437, 376-380 (2005).

Misra, A. et al. Multiplex genotyping of cytochrome p450 single-nucleotide polymorphisms by use of MALDI-TOF mass spectrometry. *Clin. Chem.* 53, 933-939 (2007).

Palacios G. et al. MassTag polymerase chain reaction for differential diagnosis of viral hemorrhagic fever. *Emerg Infect Dis.* 12(4):692-95 (2006).

Qiu, C. et al. Design and synthesis of cleavable biotinylated dideoxynucleotides for DNA sequencing by matrix-assisted laser desorption/ionization time-of-flight mass spectrometry. *Anal. Biochem.* 427, 193-201 (2012).

Qiu, C. et al. Mitochondrial single nucleotide polymorphism genotyping by matrix-assisted laser desorption/ionization time-of-flight mass spectrometry using cleavable biotinylated dideoxynucleotides. *Anal. Biochem.* 427, 202-210 (2012).

Reiner, J. E. et al. Theory for polymer analysis using nanopore-based single-molecule mass spectrometry. *Proc Natl Acad Sci USA* 107, 12080-12085 (2010).

Robertson, J. W. et al. Single-molecule mass spectrometry in solution using a solitary nanopore. *Proc Natl Acad Sci USA* 104, 8207-11 (2007).

Rodi, C. P. et al. A strategy for the rapid discovery of disease markers using the MassARRAY™ system. *Biotechniques Suppl.* 32, S62-569 (2002).

Roses, A. Pharmacogenetics and the practice of medicine. *Nature* 405, 857-865 (2000).

Ross, P. L. et al. Discrimination of single-nucleotide polymorphisms in human DNA using peptide nucleic acid probes detected by MALDI-TOF mass spectrometry. *Anal. Chem.,* 69, 4197-4202 (1997).

Roskey, M. T. et al. DNA sequencing by delayed extraction-matrix-assisted laser desorption/ionization time of flight mass spectrometry. *Proc. Natl. Acad. Sci, USA.* 93, 4724-4729 (1996).

Ross, P. et al. High level multiplex genotyping by MALDI-TOF mass spectrometry. *Nat. Biotechnol.* 16, 1347-1351 (1998).

Rothberg, J. M. et al. An integrated semiconductor device enabling non-optical genome sequencing. *Nature* 475, 348-352 (2011).

Salas-Solano, O. et al. Routine DNA sequencing of 1000 bases in less than one hour by capillary electrophoresis with replaceable linear polyacrylamide solutions. *Anal Chem.* 70, 3996-4003 (1998).

Smith, L. M. et al. Fluorescence detection in automated DNA sequencing analysis. *Nature,* 321, 674-679 (1986).

Song, L. et al. Structure of Staphylococcal alpha-hemolysin, a heptameric transmembrane pore. *Science* 274, 1859-1866 (1996).

Stoerker, J. et al. Rapid genotyping by MALDI-monitored nuclease selection from probe libraries. *Nat. Biotechnol.* 18, 1213-1216 (2000).

Tang, K. et al. Chip-based genotyping by mass spectrometry. *Proc. Natl. Acad. Sci. USA* 96, 10016-10020 (1999).

Tong, A. K. et al. Combinatorial Fluorescence Energy Transfer Tags for Multiplex Biological Assays. *Nat. Biotechnol.* 19, 756-759 (2001).

Tong, A. K. & Ju, J. Single-nucleotide Polymorphism Detection by Combinatorial Fluorescence Energy Transfer Tags and Biotinylated Dideoxynucleotides. *Nucleic Acids Research* 30, e19 (p 1-7) (2002).

Venter, J. C. et al. The sequence of the human genome. *Science* 291, 1304-1351 (2001).

Wheeler, D. A. et al. The complete genome of an individual by massively parallel DNA sequencing. *Nature* 452, 872-876 (2008).

Xiu-Cheng, F. A. et al. A rapid and accurate approach to identify single nucleotide polymorphisms of mitochondrial DNA using MALDI-TOF mass spectrometry. *Clin. Chem. Lab. Med.* 46, 299-305 (2008).

Yang, Y. et al. Advances in nanopore sequencing technology. *J. Nanosci. Nanotechnol.* 13, 4521-4538 (2013).

What is claimed is:

1. A method for identifying a single nucleotide residue of interest at a position within a stretch of consecutive nucleotide residues in a DNA, comprising the steps of:
   (a) incubating the DNA with
      (1) at least one oligonucleotide primer, each primer comprising a removably attached label (i) corresponding to a particular primer sequence, and (ii) having a unique signature detectable by a nanopore, wherein the nucleotides in the primer that are 5' to the nucleotide at the 3'-terminus of the primer are substantially fully complementary to the nucleotides in the DNA immediately 3' to the single nucleotide of interest,
      (2) terminating nucleotides, and
      (3) DNA polymerase,
   so as to perform a single base extension of a primer whose 3' terminal nucleotide hybridized to the single nucleotide residue of interest in the DNA, if such a primer was present, using the terminating nucleotide, thereby forming an extension product of the primer which had a 3' nucleotide complementary to the nucleotide of interest in the DNA;
   (b) removing the label from the extension product, if present; and
   (c) detecting with single molecule sensitivity by the nanopore the signature of the label of the primer whose 3' terminal nucleotide hybridized to the single nucleotide residue of interest, so as to identify the label and primer, if present;
   thereby identifying the single nucleotide residue of interest.

2. The method of claim 1, wherein the DNA is a single copy of a single-stranded DNA, or is a double-stranded DNA.

3. The method of claim 1, wherein in step (a) the DNA is incubated with a plurality of oligonucleotide primers, wherein the plurality of oligonucleotide primers comprises at least two primers having identical nucleotide sequences except for having a different nucleotide at the 3' terminus of each of the primers, wherein the identical nucleotides in each of the primers are substantially fully complementary to the nucleotides in the DNA immediately 3' to the single nucleotide residue of interest.

4. The method of claim 1, wherein the terminating nucleotides are dideoxynucleotides, wherein the terminating nucleotides comprise a hook, wherein the terminating nucleotides comprise a hook which is a biotin moiety, or wherein the terminating nucleotides comprise a hook which is a phenylboronic acid (PBA) moiety.

5. The method of claim 1, wherein prior to removing the label, the extension product is separated from the unextended primers, or wherein prior to removing the label, the extension product is separated from the unextended primers by capturing the extension product on streptavidin-coated magnetic beads, or wherein prior to removing the label, the extension product is separated from the unextended primers by capturing the extension product on salicylhydroxamic acid (SHA)-coated magnetic beads.

6. The method of claim 1, wherein the label is removably attached via a cleavable linker, or is removably attached via a cleavable linker which is an azido linker, or is removably attached via a cleavable linker which is cleaved in step (b) by a phosphine-containing moiety or by tris-(2-carboxyethyl)phosphine (TCEP), or is removably attached via a cleavable linker which is attached to the 5'-terminus of the oligonucleotide primer between the label and the oligonucleotide.

7. The method of claim 1, wherein the label comprises one or more of ethylene glycol, an amino acid, a carbohydrate, a peptide, a dye, a chemiluminescent compound, a mononucleotide, a dinucleotide, a trinucleotide, a tetranucleotide, a pentanucleotide, a hexanucleotide, an aliphatic acid, an aromatic acid, an alcohol, a thiol group, a cyano group, a nitro group, an alkyl group, an alkenyl group, an alkynyl group, an azido group, or a combination thereof.

8. The method of claim 1, wherein the labels are polyethylene glycol (PEG) labels, or are PEG labels which each have a different length from each other.

9. The method of claim 1, wherein the DNA is incubated with a plurality of primers, or at least 20 different oligonucleotide primers, each primer comprising an attached label having a unique signature detectable by a nanopore.

10. The method of claim 1, wherein the nanopore is biological, is proteinaceous, comprises alpha hemolysin, is a solid-state nanopore, or is in a solid-state membrane.

11. The method of claim 1, wherein the signature is an electronic signature, or is an electrical current blockade signature.

12. The method of claim 1, wherein the nucleotide sequence of the portion of each primer which is 5' to the 3' nucleotide of the primer is at least 85% complementary, is at least 90% complementary, is at least 95% complementary, or is 100% complementary to the sequence of the DNA which is 3' to the single nucleotide residue of interest.

13. The method of claim 1, wherein the sequence of the primer is 10-40 nucleotides long, or is 18-24 nucleotides long.

14. The method of claim 1, wherein the single nucleotide of interest is at the site of a single nucleotide polymorphism (SNP).

15. The method of claim 1, wherein in step (a) the DNA is incubated with a plurality of oligonucleotide primers, wherein the plurality of oligonucleotide primers comprises at least three primers having identical nucleotide sequences except for having a different nucleotide at the 3' terminus of each of the primers, wherein the identical nucleotides in each of the primers are substantially fully complementary to the nucleotides in the DNA immediately 3' to the single nucleotide residue of interest.

16. The method of claim 1, wherein in step (a) the DNA is incubated with a plurality of oligonucleotide primers, wherein the plurality of oligonucleotide primers comprises at least four primers having identical nucleotide sequences except for having a different nucleotide at the 3' terminus of each of the primers, wherein the identical nucleotides in each of the primers are substantially fully complementary to the nucleotides in the DNA immediately 3' to the single nucleotide residue of interest.

17. The method of claim 1, wherein in step (a) the DNA is incubated with a plurality of oligonucleotide primers, wherein the plurality of oligonucleotide primers comprises at least twenty primers, wherein the 3' nucleotide of each primer is complementary to a single nucleotide residue of interest in the DNA and the other nucleotides in each primer are substantially fully complementary to the nucleotides in the DNA immediately 3' to the single nucleotide residue of interest.

18. A method for simultaneously detecting in a sample the presence of one or more of a plurality of different target nucleic acids comprising the steps of:
 (a) contacting the sample with a plurality of nucleic acid primers simultaneously and under conditions permitting, and for a time sufficient for, primer extension to occur, wherein (i) for each target nucleic acid at least one predetermined primer is used which corresponds to that target nucleic acid, and (ii) each primer has a removably attached label having a unique signature detectable by a nanopore;
 (b) separating any unextended primers from any extended primers;
 (c) simultaneously removing the labels from any extended primers; and
 (d) detecting with single molecule sensitivity by the nanopore the presence of any labels so removed;
wherein the presence of a removed label having a signature identical to the label removably attached to a predetermined primer indicates the presence in the sample of the target nucleic acid specifically recognized by that predetermined primer.

* * * * *